(12) United States Patent
Beall

(10) Patent No.: US 9,228,008 B2
(45) Date of Patent: Jan. 5, 2016

(54) CANINE ANTI-CD20 ANTIBODIES

(75) Inventor: Melissa J. Beall, Cape Elizabeth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 365 days.

(21) Appl. No.: 12/941,583

(22) Filed: Nov. 8, 2010

(65) Prior Publication Data

US 2011/0091483 A1 Apr. 21, 2011

Related U.S. Application Data

(60) Continuation-in-part of application No. 11/828,464, filed on Jul. 26, 2007, which is a division of application No. 11/138,949, filed on May 26, 2005, now Pat. No. 7,531,628.

(60) Provisional application No. 61/258,647, filed on Nov. 6, 2009, provisional application No. 60/575,172, filed on May 28, 2004.

(51) Int. Cl.
*C07K 16/28* (2006.01)
*C07K 16/30* (2006.01)
*C12N 5/20* (2006.01)
*C07K 14/705* (2006.01)
*C12N 5/16* (2006.01)
*A61K 39/395* (2006.01)
*G01N 33/50* (2006.01)
*G01N 33/564* (2006.01)

(52) U.S. Cl.
CPC ..... *C07K 14/70596* (2013.01); *A61K 39/39541* (2013.01); *A61K 39/39558* (2013.01); *C07K 16/2887* (2013.01); *C07K 16/3061* (2013.01); *C12N 5/163* (2013.01); *G01N 33/5052* (2013.01); *G01N 33/564* (2013.01); *C07K 2317/33* (2013.01)

(58) Field of Classification Search
CPC ............................ C07K 16/2887; C12N 5/163
See application file for complete search history.

(56) References Cited

U.S. PATENT DOCUMENTS

| | | |
|---|---|---|
| 5,593,861 A | 1/1997 | Maeda et al. |
| 5,849,898 A | 12/1998 | Seed et al. |
| 7,151,164 B2 | 12/2006 | Hansen et al. |
| 7,531,628 B2 | 5/2009 | Beall |
| 2002/0041847 A1 | 4/2002 | Goldenberg |
| 2003/0129696 A1 | 7/2003 | Ni et al. |
| 2003/0228326 A1 | 12/2003 | Palomba et al. |
| 2005/0048071 A1 | 3/2005 | Bae |
| 2005/0238650 A1 | 10/2005 | Crowley et al. |
| 2005/0271662 A1 | 12/2005 | Beall |
| 2008/0045700 A1 | 2/2008 | Beall |
| 2011/0217298 A1 | 9/2011 | Hansen |

FOREIGN PATENT DOCUMENTS

| | | |
|---|---|---|
| WO | 02/062946 A2 | 8/2002 |
| WO | 2006/062946 A2 | 8/2002 |
| WO | 03/068821 A2 | 8/2003 |
| WO | 2004/035607 A2 | 4/2004 |
| WO | 2005/075640 A1 | 8/2005 |
| WO | 2006/007202 A2 | 1/2006 |
| WO | WO 2006/007202 A2 * | 1/2006 |
| WO | 2010/027488 A2 | 3/2010 |
| WO | 2010/117448 A2 | 10/2010 |

OTHER PUBLICATIONS

De Pascalis et al., "Grafting of "Abbreviated" Complementarity-Determining Regions Containing Specificity-Determining Residues Essential for Ligand Contact to Engineer a Less Immunogenic Humanized Monoclonal Antibody",The Journal of Immunology, 2002, 169: 3076-3084.*
MacCallum et al. "Antibody-antigen Interactions: Contact Analysis and Binding Site Topography", J. Mol. Biol. (1996) 262, 732-745.*
Coyle et al., "Characterizaiton of Lymphocytes in Canine Gastrointestinal Lymphoma," Vet. Pathol., 41(2):141-146 (Mar. 1, 2004).
Stamenkovic et la., "Analysis of Two cDNA Clones Encoding the B Lymphocyte Antigen CD20, (B1, Bp35), a Type III Integral Membrane Protein," J. Exp. Med., vol. 167, 1975-1980 (1988).
Rastetter et al., "Rituximab: Expanding Role in therapy for Lymphomas and autoimmune Diseases," Annu. Rev. Med., 55:477-503 (2004).
Jubala et al., "CD20 Expression in Normal Canine B Cells and in Canine non-Hodgkin Lymphoma," Vet. Pathol., 42:468-476 (2005).
Kano et al., "Canine CD20 Gene," Veterinary Immunology and Immunopathology, 108(3-4):265-368 (Dec. 15, 2005).
Polyak et al., "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," Blood, 99(9):3256-3262 (2002).
Crow, "Chemoimmunotherapy for canine lymphoma: tumor vaccines and monoclonal antibodies," Cancer Therapy, 6:181-186 (2008).
Impellizeri et al., "The role of rituximab in the treatment of canine lymphoma: An ex vivo evaluation," The Veterinary Journal 171(3):556-558 (May 1, 2006).
Galkowska et al, "Reactivity of antibodies directed against human antigens with surface markers on canine leukocytes," Veterinary Immunology and Immunopathology, 53:329-334 (1996).
Brodersen et al., "Analysis of the immunological cross reactivities of 213 well characterized monoclonal antibodies with specificities against various leucocyte surface antigens of human and 11 animal species," Veterinary Immunology and Immunopathology, 64:1-13 (1998).
Wunderli et al., "An Improved Method for Isolation of Enriched Canine Peripheral Blood Mononuclear Cell and Peripheral Blood Lymphocyte Preparations," Veterinary Immunology and Immunopathology, 29:335-344 (1989).
Chabanne et al., "Screening of 78 monoclonal antibodies directed against human leukocyte antigens for cross-reactivity with surface markers on canine lymphocytes," Tissue Antigens, 43:202-205 (1994).

(Continued)

*Primary Examiner* — Ronald Schwadron
(74) *Attorney, Agent, or Firm* — McDonnell Boehnen Hulbert & Berghoff LLP

(57) ABSTRACT

The invention provides canine CD20 specific antibodies, methods of making the antibodies and methods of use of the antibodies.

12 Claims, 1 Drawing Sheet

(56) References Cited

OTHER PUBLICATIONS

Greenlee et al., Investigation of Cross-Reactivity between Commercially Available Antibodies Directed Against Human, Mouse, and Rat Lymphocyte Surface Antigens and Surface Markers on Canine Cells, Veterinary Immunology and Immunopathology, 15:285-296 (1987).
Schuberth et al., "Reactivity of cross-reacting monoclonal antibodies with canine leukocytes, platelets and erythrocytes," Veterinary Immunology and Immunopathology, 119:47-55 (2007).
Jensen-Jarolim et al., "Small mimotypes are big in identifying B-cell epitopes," Blood Journal, 108(6):1794 (2006).
GenBank Accession No. L77424, dated Apr. 9, 1996.
GenBank Accession No. L77425, dated Apr. 9, 1996.
Venta et al., "Gene-specific universal mammarian sequence-tagged sites: application to the canine genome," Biochemical Genetics, 34(7-8):321-341 (1996).
Tang et al., "Cloning and characterization of cDNAs encoding four different canine immunoglobulin γ chains," Veterinary Immunology and Immunopathology, 80:259-270 (2001).
Press O.W. et al., "Monoclonal Antibody 1F5 Anti-CD20 Serotherapy of Human B Cell Lymphomas," Blood, 89 (2):584-591 (1987).
Leonard et al., "New monoclonal antibodies for non-Hodgkin's lymphoma," Annals of Oncology 19 (Supplement 4): iv60-iv62 (2008).
Lee et al., "A Hospital-Based Serological Survey of Cryptosporidiosis in the Republic of Korea," Korean J. Parasitol., 47(3):219-225 (Sep. 2009).
Ragnhammar et al., "Induction of Anti-Recombinant Human Granulocyte-Macrophage Colony-Stimulating Factor (*Escherichia coli*-Derived) Antibodies and Clinical Effects in Nonimmunocompromised Patients," Blood, 84 (12):4078-4087 (Dec. 15, 1994).
Ohano et al., UniProt KB/Trembl Accession No. Q5R1M8, Jul. 24, 2007.
Moore et al., UniProt KB/Trembl Accession No. Q17QX1, Jul. 24, 2007.
Tedder et al., "Isolation and structure of a cDNA encoding the B1 (CD20) cell-surface antigen of human B. lymphocytes," Proc. Natl. Acad. Sci. USA, 85:208-212 (Jan. 1988).
Einfeld et al., "Molecular cloning of the human B cell CD20 receptor predicts a hydrophobic protein with multiple transmembrane domains," EMBO J., 7:711-717 (1988).
Tedder et al., "Structure of the gene encoding the human B lymphocyte differentiation antigen CD20 (B1)," J. Immunol., 142:2560-2568 (1989).

The MGC Project Team, "The status, quality, and expansion of the NIH full-length cDNA project: the Mammalian Gene Collection (MCG)," Genome Res., 14:2121-2127 (2004).
Wakamatsu et al., UniProtKB/Trembl Accession No. A8K83, Dec. 4, 2007.
Taylor et al., "Human chromosome 11 DNA sequence and analysis including novel gene identification," Nature, 440:497-500 (2006).
Certificate of Accuracy of translation of WO 2005/075640 Dec. 9, 2005.
English translation of Kano et al., Japanese Patent No. PCT/JP2005/001880; International Publication No. WO 2005/075640A1, international publication date Aug. 18, 2005.
International Search Report for corresponding PCT application serial No. PCT/US2005/018515 dated May 17, 2006, Idexx Labs, filed May 26, 2005.
Office action dated Oct. 3, 2007, from US 2005/0271662; published Dec. 8, 2005; Inventor: Beall, U.S. Appl. No. 11/138,949 Beall,"Canine CD20 Compositions", filed May 26, 2005.
Office action dated Apr. 8, 2008 from US 2005/0271662; published Dec. 8, 2005; Inventor: Beall, U.S. Appl. No. 11/138,949 Beall, "Canine CD20 Compositons", filed May 26, 2005.
Final office action for U.S. Appl. No. 11/828,464, mailed Dec. 7, 2010, U.S. Appl. No. 11/828,464 Beall, Canine CD20 Compositons, filed May 26, 2005.
Final office action for U.S. Appl. No. 11/828,464, mailed May 5, 2009, U.S. Appl. No. 11/828,464 Beall, Canine CD20 Compositons, filed May 26, 2005.
Non-final office action for U.S. Appl. No. 11/828,464, mailed Mar. 5, 2008, U.S. Appl. No. 11/828,464 Beall, Canine CD20 Compositons, filed May 26, 2005.
Non-final office action for U.S. Appl. No. 11/828,464, mailed Sep. 16, 2009, U.S. Appl. No. 11/828,464 Beall, Canine CD20 Compositons, filed May 26, 2005.
WebMD, "Immunoglobulins", http://www.webmd.com/a-to-zguides/immunoglobulins?print=true, May 4, 2009.
International Search Report for application No. PCT/US2010/055826 dated Jan. 19, 2011, Idexx Labs, filed Nov. 8, 2010.
Letter to Conan Deady, Vice President General Counsel and Secretary of IDEXX Laboratories from Steve P. Hassid from Greenberg Traurig dated Feb. 4, 2008.
Office action for U.S. Appl. No. 11/828,464 dated Dec. 17, 2014, Beall, "Canine CD20 Compositions", filed May 26, 2005.
Final office action for U.S. Appl. No. 11/828,464 dated Feb. 24, 2012, Beall, "Canine CD20 Compositions", filed May 26, 2005.
Office action for U.S. Appl. No. 11/828,464 dated Jul. 19, 2011, Beall, "Canine CD20 Compositions", filed May 26, 2005.

\* cited by examiner

Monoclonal antibody 6C8

CANINE ANTI-CD20 ANTIBODIES

PRIORITY

This application claims the benefit of U.S. Ser. No. 61/258, 647, filed Nov. 6, 2009. This application also claims priority to U.S. Ser. No. 11/828,464, filed on Jul. 26, 2007, which is a divisional application of U.S. Ser. No. 11/138,949, filed May 26, 2005 (now U.S. Pat. No. 7,531,628), which claims the benefit of U.S. Ser. No. 60/575,172, filed on May 28, 2004. These applications are incorporated by reference in their entirety herein.

SEQUENCE LISTING

This document incorporates by reference herein an electronic sequence listing text file, which is filed in electronic format via EFS-Web. The text file is named "09373ST25.txt" is 19,279 bytes, and was created on Dec. 22, 2010.

BACKGROUND OF THE INVENTION

CD20 is a transmembrane protein that is expressed on more than 95% of B-lymphocytes. Expression at the cell surface occurs from the pre-B stage of development until differentiation to a plasma cell. In human medicine, an anti-CD20 monoclonal antibody therapeutic (e.g., Rituximab) has been used to treat relapsed or refractory non-Hodgkin's lymphoma (NHL), as a first-line therapy for NHL as well as diffuse large B-cell lymphoma, and as an adjunct therapy for NHL. Although expression of CD20 has been shown to correlate with B-cell lymphoma in the dog (Jubala et al., Vet. Path., (2005) 42:468-76), the human therapeutic is not able to bind or deplete canine B-cells ex vivo (Impellizeri et al., Vet. J. (2006) 171:556-8). Therefore, compositions and methods of treatment of B-cell lymphoma, rheumatoid arthritis, immune-mediated hemolytic anemia, immune-mediated thrombocytopenia, systemic lupus erythematosus, autoimmune disease, or other diseases that are characterized by the presence of too many B cells, overactive or over-expressed B cells or dysfunctional B cells are needed in the dog.

SUMMARY OF THE INVENTION

One embodiment of the invention provides an isolated antibody or antigen-binding portion thereof that specifically binds canine CD20, wherein said antibody binds the same canine CD20 epitope recognized by the monoclonal antibody produced by the hybridoma cell line having ATCC number PTA-9433 (4F1), ATCC number PTA-9434 (6C8), ATCC number PTA-9435 (14A12), ATCC number PTA-9436 (18D3). The antibody can comprise a VH CDR1 of SEQ ID NO:9, 12, 15 or 18; a VH CDR2 of SEQ ID NO:10, 13, 16, or 19; a VH CDR3 of SEQ ID NO:11, 14, 17, or 20; a VL CDR1 of SEQ ID NO:21, 24, 27, or 30; a VL CDR2 of SEQ ID NO:22, 25, 28, or 31; and a VL CDR3 of SEQ ID NO:23, 26, 29, or 32.

Another embodiment of the invention provides an isolated antibody or antigen-binding portion thereof, wherein said antibody or antigen-binding portion specifically binds canine CD20, wherein the antibody or antigen-binding portion thereof competes for binding with a monoclonal antibody produced by the hybridoma cell line having ATCC number PTA-9433 (4F1), ATCC number PTA-9434 (6C8), ATCC number PTA-9435 (14A12), ATCC number PTA-9436 (18D3) to canine CD20. The antibody or antigen-binding portion thereof can inhibit the binding of a monoclonal antibody produced by the hybridoma cell line having ATCC number PTA-9433 (4F1), ATCC number PTA-9434 (6C8), ATCC number PTA-9435 (14A12), ATCC number PTA-9436 (18D3) to canine CD20. The antibody or antigen-binding portion thereof can specifically bind to canine lymphocytes. The antibody or antigen-binding portion thereof can specifically bind to a polypeptide consisting of an amino acid sequence of SEQ ID NO:36. The antibody or antigen-binding portion thereof can specifically bind to a polypeptide comprising an amino acid sequence of SEQ ID NO:36, while not specifically binding to a polypeptide consisting of an amino acid sequence of SEQ ID NO:35.

Antibodies or antigen-binding portions thereof can be a monoclonal antibody, a polyclonal antibody, a chimeric antibody, a humanized antibody, a synthetic antibody, a single chain antibody, a diabody, a caninized antibody, a canine antibody, a human antibody, or a CDR-grafted antibody. Antibodies or antigen-binding portions thereof can be IgG1, IgG2, IgG2a, IgG2b, IgG3, or IgG4.

Yet another embodiment of the invention provides an antibody or antigen-binding portion thereof that comprises a VL amino acid sequence of SEQ ID NO:5, 6, 7, or 8 or a VH amino acid sequence of SEQ ID NO:1, 2, 3, or 4.

Still another embodiment of the invention provides a composition comprising an antibody or antigen-binding portion of the invention and a pharmaceutically acceptable carrier.

Even another embodiment of the invention provides antibodies or antigen-binding portions thereof that specifically bind canine CD20 with an affinity ($K_d$) of at least about $10^{-6}$ M.

Another embodiment of the invention provides antibodies or antigen-binding portions thereof that induce apoptosis of CD20+ cells.

Yet another embodiment of the invention provides antibodies or antigen-binding portions thereof that comprise the same heavy and light chain polypeptide sequences as an antibody produced by hybridoma ATCC number PTA-9433 (4F1), ATCC number PTA-9434 (6C8), ATCC number PTA-9435 (14A12), or ATCC number PTA-9436 (18D3).

Still another embodiment of the invention provides antibodies or antigen-binding portions thereof wherein the antibody is produced by the hybridoma cell line having ATCC number PTA-9433 (4F1), ATCC number PTA-9434 (6C8), ATCC number PTA-9435 (14A12), ATCC number PTA-9436 (18D3).

Even another embodiment of the invention provides an isolated cell of hybridoma ATCC number PTA-9433 (4F1), ATCC number PTA-9434 (6C8), ATCC number PTA-9435 (14A12), or ATCC number PTA-9436 (18D3).

Another embodiment of the invention provides an isolated polypeptide comprising SEQ ID NO:1-36 and polynucleotides that encode the polypeptides comprising SEQ ID NO:1-36.

Yet another embodiment of the invention provides an isolated polynucleotide encoding an anti-canine CD20 antibody or antigen-binding portion thereof, wherein said isolated polynucleotide encodes a heavy chain and a light chain, wherein the immunoglobulin heavy chain complementarity determining region (CDR) CDR1 comprises SEQ ID NO:9, 12, 15, or 18, the CDR2 comprises SEQ ID NO:10, 13, 16, or 19, and the CDR3 comprises SEQ ID NO:11, 14, 17 or 20, and wherein the immunoglobulin light chain CDR1 comprises SEQ ID NO:21, 24, 27, or 30, the CDR2 comprises SEQ ID NO:22, 25, 28, or 31, and the CDR3 comprise SEQ ID NO:23, 26, 29 or 32.

Still another embodiment of the invention provides a vector comprising one or more polynucleotides of the invention.

Even another embodiment of the invention provides a host cell comprising a vector of the invention.

Another embodiment of the invention provides a method for producing a canine anti-CD20 antibody or antigen-binding portion thereof, comprising culturing an isolated host cell of the invention and recovering said antibody.

Yet another embodiment of the invention provides an isolated antibody or antigen-binding portion thereof that specifically binds to canine CD20, wherein the antibody or antigen-binding portion thereof comprises a heavy chain and a light chain variable domain, wherein the antibody or antigen-binding portion thereof comprises six complementarity determining regions (CDRs), and wherein three of the six CDRs comprise amino acid sequences wherein the antibody variable heavy chain CDRs are selected from SEQ ID NOs:9-20 and wherein the antibody variable light chain CDRs are selected from SEQ ID NOs:21-32.

DETAILED DESCRIPTION OF THE INVENTION

Figure 1A:
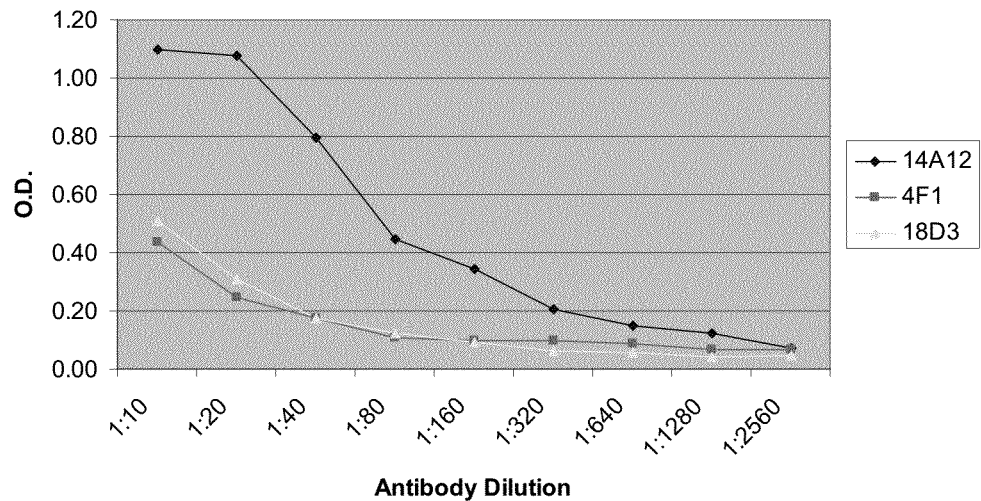
FIG. 1A-B shows the results of a canine CD20-peptide ELISA using antibodies produced by hybridomas 6C8, 4F1, 14A12, and 18D3.

As used herein, the singular forms "a," "an," and "the" include plural referents unless the context clearly dictates otherwise.

Polypeptides

A polypeptide is a polymer of three or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

A light or heavy chain variable region of an antibody has four framework regions interrupted by three hypervariable regions, known as complementary determining regions (CDRs). CDRs determine the specificity of antigen binding. The heavy chain and light chain each have three CDRs, designated from the N terminus as CDR1, CDR2, and CDR3 with the four framework regions flanking these CDRs. The amino acid sequences of the framework region are highly conserved and CDRs can be transplanted into other antibodies. Therefore, a recombinant antibody can be produced by combining CDRs from one or more antibodies with the framework of one or more other antibodies. Antibodies of the invention include antibodies that comprise at least one, two, three, four, five, or six (or combinations thereof) of the CDRs of any of the monoclonal antibodies isolated from the hybridomas shown in Table 1, or variant CDRs. Variant CDRs are CDRs comprising amino acid sequences similar to the amino acid sequences of CDRs of any of the monoclonal antibodies produced by the hybridomas shown in Table 1. In one embodiment of the invention variant CDRs specifically bind to canine CD20 when present in an appropriate antibody structure (e.g., framework regions and other appropriate CDRs).

Polypeptides of the invention comprise full-length canine anti-CD20 heavy chain variable regions, full length canine anti-CD20 light chain regions, fragments thereof, and combinations thereof. Canine anti-CD20 heavy chain variable regions for antibodies 6C8, 4F1, 14A12, and 18D3 (see Examples) are shown below:

```
6C8      MGWSYIXXFLVATATDVHSQVQLQQPGAELVKPGASVKLSCKA          43

4F1      MXXXWVIXFLMAXVTGVNSEVQLQQSGAEVVKXGASVKLSCTT          43

14A12    -----SLLYLLTALPGILSEVQLQESGPSLVKPSQTLSLTCSV          38

18D3     MXWSWVXLFLVATAIGVHSQVQLQQSGAELVKPGASVKMSCKA          43

6C8      SGYIFTTYWMNWVKQRPGQGLEWIGEISPEDGRINYNEKEKNKATLTVDK   93

4F1      XGFNIKDTYIHWVKQRPEQGLEWIGRIDPANGYTKYDPEFQGKAXITAGT   93

14A12    TGDSITSGYWNWIRQFPGNKLEYMGYIS-YSGITYYNPSLKSRISITRDT   87

18D3     FGYTFTTYPIEWMKQNHGKSLEWIGNFHPYNDDTKYNEKFKGKAKLTVEK   93

6C8      SSSTAYMQLSSLTSEDSAVYYCAR---D-----------SYWGQGTLVTV   129

4F1      SSNTAYLQLSSLTSEDTAVYYCARWGNGNPYY---Y-AMDYWGQGTSVTX   139

14A12    SKNQYYLQLNSLTTEDTATYYCARSLYD-------YVGFAYWGQGTLVTV   130

18D3     SSSTVYLELSRLTSDDSAVYYCAM-----GYY------FDYWGQGTTLTV   132

6C8      SAAKTTPPSVYPLXPGSLGRAN                               151

4F1      SSATTTAPXVYPLXPGSLG                                  158

14A12    SAAKTTPPXVYXLXPGSL                                   148

18D3     SSAKTTPPXVYPLVPGSLGRAN                               154
```

SEQ ID NO:1 6C8 heavy chain variable region.
SEQ ID NO:2 4F1 heavy chain variable region.
SEQ ID NO:3 14A12 heavy chain variable region.
SEQ ID NO:4 18D3 heavy chain variable region.
The X at position 7 of SEQ ID NO:1 can be I or M.
The X at position 8 of SEQ ID NO:1 can be L or F.
The X at position 143 of SEQ ID NO:1 can be A or V.
The X at position 2 of SEQ ID NO:2 can be E or K.
The X at position 3 of SEQ ID NO:2 can be C or W.
The X at position 4 of SEQ ID NO:2 can be S or T.
The X at position 8 of SEQ ID NO:2 can be L or F.
The X at position 13 of SEQ ID NO:2 can be M or V.
The X at position 33 of SEQ ID NO:2 can be P or S.
The X at position 44 of SEQ ID NO:2 can be S or P.
The X at position 88 of SEQ ID NO:2 can be I or T.
The X at position 139 of SEQ ID NO:2 can be V or A.
The X at position 148 of SEQ ID NO:2 can be S or P.
The X at position 153 of SEQ ID NO:2 can be A or V.
The X at position 139 of SEQ ID NO:3 can be S or P.
The X at position 142 of SEQ ID NO:3 can be P or Q.
The X at position 144 of SEQ ID NO:3 can be A or V.
The X at position 2 of SEQ ID NO:4 can be E or K.
The X at position 7 of SEQ ID NO:4 can be I or F.
The X at position 141 of SEQ ID NO:4 can be S or P.
SEQ ID NO:9 6C8 heavy chain CDR1 (amino acids 46 to 54 of SEQ ID NO:1).
SEQ ID NO:10 6C8 heavy chain CDR2 (amino acids 69 to 85 of SEQ ID NO:1).
SEQ ID NO:11 6C8 heavy chain CDR3 (amino acids 118 to 120 of SEQ ID NO:1).
SEQ ID NO:12 4F1 heavy chain CDR1 (amino acids 46 to 54 of SEQ ID NO:2).
SEQ ID NO:13 4F1 heavy chain CDR2 (amino acids 69 to 85 of SEQ ID NO:2).
SEQ ID NO:14 4F1 heavy chain CDR3 (amino acids 118 to 130 of SEQ ID NO:2).
SEQ ID NO:15 14A12 heavy chain CDR1 (amino acids 41 to 49 of SEQ ID NO:3).
SEQ ID NO:16 14A12 heavy chain CDR2 (amino acids 64 to 79 of SEQ ID NO:3).
SEQ ID NO:17 14A12 heavy chain CDR3 (amino acids 112 to 121 of SEQ ID NO:3).
SEQ ID NO:18 18D3 heavy chain CDR1 (amino acids 46 to 54 of SEQ ID NO:4).
SEQ ID NO:19 18D3 heavy chain CDR2 (amino acids 69 to 85 of SEQ ID NO:4).
SEQ ID NO:20 18D3 heavy chain CDR3 (amino acids 118 to 123 of SEQ ID NO:4).

Canine anti-CD20 light chains variable regions for 6C8, 4F1, 14A12, and 18D3 (see Examples) are shown below:

```
6C8                           DXVMSQSPSSLAVSL--GEKITMSC        23
4F1                           DIVMSQSPSSLAVSV--GEKVTVSC        23
14A12     LVDMDFQVQIISFLLISASGQIVLTQSPAI-MSASPGERVTVTF         43
18D3         MAWXXLXXSLLALSSGAISQAVVTQESALTTSPGETVTLTC         41

6C8     KSSQSLLYSSNQKSYLA-WYQQKPGQSPELLIYWASTRDXGVPDRFTGXGS    73
4F1     KSSQTLLXSSNQKNYLA-WYQQKPGQSPNLLIYSASTRESGVPDRFTGSGS    73
14A12   SARSSVR-SS----YL-YLYQQKPGSSPKLWIYSTSNLASGVPARFSGSGS    88
18D3    RSSTGAVTTS---N-YANWVQEKPDHLFTGLIGGTNNRAPGVPARFSGSLI    88

6C8     GTDFTLTISSVKAEDLAVXFCQQYYTYPYTFGGGTKLEIKRA            115
4F1     GTDFTLTISNLKAEDLAVYYCQQYYSYPLTFGAGTKLELKRA            115
14A12   GTSYSLTISSMETEDAATFYCQQYSGYPSRSVLGPSWS                126
18D3    GDKAALTITGAQTEDEAIYFCALWYSNHWVFGGGTKLTVLGQ            130

6C8     DAAPTVSIFPPSSKLG                                      131
4F1     DAAPTVSIFPPSSKLGKGE                                   134
14A12
18D3    PKSSPSVTLFPPSTEELSL                                   149
```

SEQ ID NO:5 6C8 light chain variable region.
SEQ ID NO:6 4F1 light chain variable region.
SEQ ID NO:7 14A12 light chain variable region.
SEQ ID NO:8 18D3 light chain variable region.
The X at position 2 of SEQ ID NO:5 can be I or T.
The X at position 62 of SEQ ID NO:5 can be S or P.
The X at position 71 of SEQ ID NO:5 can be G or S.
The X at position 92 of SEQ ID NO:5 can be H or Y.
The X at position 31 of SEQ ID NO:6 can be C or Y.
The X at position 4 of SEQ ID NO:8 can be I or T.
The X at position 5 of SEQ ID NO:8 can be P or S.
The X at position 7 of SEQ ID NO:8 can be I or L.
The X at position 8 of SEQ ID NO:8 can be F or L.
SEQ ID NO:21 6C8 light chain CDR1 (amino acids 24 to 40 of SEQ ID NO:5).
SEQ ID NO:22 6C8 light chain CDR2 (amino acids 56 to 62 of SEQ ID NO:5).
SEQ ID NO:23 6C8 light chain CDR3 (amino acids 95 to 103 of SEQ ID NO:5).
SEQ ID NO:24 4F1 light chain CDR1 (amino acids 24 to 40 of SEQ ID NO:6).
SEQ ID NO:25 4F1 light chain CDR2 (amino acids 56 to 62 of SEQ ID NO:6).
SEQ ID NO:26 4F1 light chain CDR3 (amino acids 95 to 103 of SEQ ID NO:6).
SEQ ID NO:27 14A12 light chain CDR1 (amino acids 44 to 54 of SEQ ID NO:7).

SEQ ID NO:28 14A12 light chain CDR2 (amino acids 71 to 77 of SEQ ID NO:7).
SEQ ID NO:29 14A12 light chain CDR3 (amino acids 110 to 118 of SEQ ID NO:7).
SEQ ID NO:30 18D3 light chain CDR1 (amino acids 42 to 54 of SEQ ID NO:8).
SEQ ID NO:31 18D3 light chain CDR2 (amino acids 71 to 77 of SEQ ID NO:8).
SEQ ID NO:32 18D3 light chain CDR3 (amino acids 110 to 118 of SEQ ID NO:8).

An antibody of the invention can comprise a VH (variable heavy chain) of SEQ ID NOs:1, 2, 3, or 4. An antibody of the invention can comprise a VL (variable light chain) of SEQ ID NOs:5, 6, 7, or 8. An antibody can comprise a VH CDR1 of SEQ ID NOs:9, 12, 15, or 18. An antibody of the invention can comprise a VH CDR 2 of SEQ ID NOs:10, 13, 16, or 19. An antibody of the invention can comprise a VH CDR 3 of SEQ ID NOs:11, 14, 17, or 20. An antibody of the invention can comprise a VL CDR 1 of SEQ ID NOs:21, 24, 27, or 30. An antibody of the invention can comprise a VL CDR 2 of SEQ ID NOs:22, 25, 28, or 31. An antibody of the invention can comprise a VL CDR 3 of SEQ ID NOs:23, 26, 29 or 32. An antibody of the invention can comprise a VH CDR 1 of any of SEQ ID NOs:9, 12, 15 or 18; a VH CDR2 of any of SEQ ID NOs: 10, 13, 16 or 19; a VH CDR3 of any of SEQ ID NOs: 11, 14, 17 and 20; a VL CDR1 of any of SEQ ID NOs:21, 24, 27, or 30; a VL CDR2 of any of SEQ ID NOs:22, 25, 28, or 31; and a VL CDR 3 of any of SEQ ID NOs:23, 26, 29, or 32 or any combination thereof.

An antibody of the invention can comprise a VH of SEQ ID NO:1 and a VL of SEQ ID NO:5. An antibody of the invention can comprise a VH of SEQ ID NO:2 and a VL of SEQ ID NO:6. An antibody of the invention can comprise a VH of SEQ ID NO:3 and a VL of SEQ ID NO:7. An antibody of the invention can comprise a VH of SEQ ID NO:4 and a VL of SEQ ID NO:8.

An antibody of the invention can comprise a VH CDR1 of SEQ ID NO:9, a VH CDR2 of SEQ ID NO:10; and a VH CDR3 of SEQ ID NO:11. An antibody of the invention can comprise a VH CDR1 of SEQ ID NO:12, a VH CDR2 of SEQ ID NO:13; and a VH CDR3 of SEQ ID NO:14. An antibody of the invention can comprise a VH CDR1 of SEQ ID NO:15, a VH CDR2 of SEQ ID NO:16; and a VH CDR3 of SEQ ID NO:17. An antibody of the invention can comprise a VH CDR1 of SEQ ID NO:18, a VH CDR2 of SEQ ID NO:19; and a VH CDR3 of SEQ ID NO:20. An antibody of the invention can comprise a VL CDR1 of SEQ ID NO:21, a VL CDR2 of SEQ ID NO:22, a VL CDR3 of SEQ ID NO:23. An antibody of the invention can comprise a VL CDR1 of SEQ ID NO:24, a VL CDR2 of SEQ ID NO:25, a VL CDR3 of SEQ ID NO:26. An antibody of the invention can comprise a VL CDR1 of SEQ ID NO:27, a VL CDR2 of SEQ ID NO:28, a VL CDR3 of SEQ ID NO:29. An antibody of the invention can comprise a VL CDR1 of SEQ ID NO:30, a VL CDR2 of SEQ ID NO:31, a VL CDR3 of SEQ ID NO:32. An antibody of the invention may have any of the above VHs combined with any of the above VLs. An antibody of the invention can have any combination of VH CDR1, VH CDR2, VH CDR3, VL CDR1, VL CDR2, VL CDR3, variant VH CDR1, variant VH CDR2, variant VH CDR3, variant VL CDR1, variant VL CDR2, or variant VL CDR3. In one embodiment of the invention an antibody comprises a VH of SEQ ID NOs:1-4 (or a variant thereof) and at least one, two or three VL CDRs of SEQ ID NOs:21-32 (or a variant thereof). In one embodiment of the invention an antibody comprises a VL of SEQ ID NOs:5-8 (or a variant thereof) and at least one, two or three VH CDRs of SEQ ID NOs:9-20 (or a variant thereof).

An antibody of the invention can comprise the variable heavy chain CDRs from antibody 6C8, 4F1, 14A12, or 18D3. An antibody of the invention can comprise the variable light chain CDRs from antibody 6C8, 4F1, 14A12, or 18D3. An antibody of the invention can comprise a variable light chain that comprises the amino acid sequence of at least one or at least two or at least 3 CDRs of the 6C8, 4F1, 14A12, or 18D3 antibody variable light chains. An antibody of the invention can comprise a variable heavy chain that comprises the amino acid sequence of at least one or at least two or at least 3 CDRs of the 6C8, 4F1, 14A12, or 18D3 antibody variable heavy chains.

Heavy chain CDRs can be combined with appropriate variable regions of an antibody light chain. Light chain CDRs preferably combined with heavy chain CDRs are, for example, CDRs comprising SEQ ID NOs:21-32, or CDRs functionally equivalent to these CDRs. The respective amino acid sequences correspond to CDR1 (SEQ ID NOs:21, 24, 27, and 30), CDR2 (SEQ ID NO:22, 25, 28, and 31), and CDR3 (SEQ ID NO:23, 26, 29, and 32) of an antibody light chain. Alternatively, these light chain CDRs may be used independently of the heavy chains described above. The CDRs are substituted for the corresponding CDR1, CDR2, and CDR3, between the framework of a desired light chain variable region.

Light chain CDRs can be combined with appropriate variable regions of an antibody heavy chain. Heavy chain CDRs preferably combined with light chain CDRs are, for example, CDRs comprising SEQ ID NOs:9-20, or CDRs functionally equivalent to these CDRs. The respective amino acid sequences correspond to CDR1 (SEQ ID NOs:9, 12, 15, and 18), CDR2 (SEQ ID NO:10, 13, 16, and 19), and CDR3 (SEQ ID NO:11, 14, 17, and 20) of an antibody light chain. Alternatively, these heavy chain CDRs may be used independently of the light chains described above. The CDRs are substituted for the corresponding CDR1, CDR2, and CDR3 regions, between the framework of a desired heavy chain variable region.

A polypeptide variant or variant CDR differs by about, for example, 1, 2, 3, 4, 5, 6, 7, 8, 9, 10, 20, 30, 40, 50, 60 or more amino acid residues (e.g., amino acid additions, substitutions or deletions) from a polypeptide shown in SEQ ID NOs:1-32 or a fragment thereof. Where this comparison requires alignment the sequences are aligned for maximum homology. The site of variation can occur anywhere in the polypeptide. In one embodiment of the invention a variant polypeptide has activity substantially similar to a polypeptide shown in SEQ ID NOs:1-32. Activity substantially similar means that when the polypeptide is used to construct an antibody, the antibody has the same or substantially the same activity as an antibody shown in Table 1.

Methods of introducing a mutation into an amino acid sequence are well known to those skilled in the art. See, e.g., Ausubel (ed.), Current Protocols in Molecular Biology, John Wiley and Sons, Inc. (1994); Maniatis et al., Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene). The generation of a functionally active variant polypeptide by replacing an amino acid that does not influence the function of a polypeptide can be accomplished by one skilled in the art.

The variant polypeptides can have conservative amino acid substitutions at one or more predicted non-essential amino acid residues. A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant polypeptide can also be isolated using a hybridization technique. Briefly, DNA having a high homology to the whole or part of a nucleic acid sequence encoding SEQ ID NOs:1-36 is used to prepare a polypeptide. Therefore, a polypeptide of the invention also includes polypeptides that are variants of SEQ ID NOs:1-36 polypeptides and are encoded by a nucleic acid molecule that hybridizes with a nucleic acid encoding SEQ ID NOs:1-36 or a complement thereof. One of skill in the art can easily determine nucleic acid sequences that encode polypeptides of the invention using readily available codon tables. As such, these nucleic acid sequences are not presented herein.

As used herein, percent identity of two amino acid sequences (or of two nucleic acid sequences) is determined using the algorithm of Karlin and Altschul (PNAS USA 87:2264-2268, 1990), modified as in Karlin and Altschul, PNAS USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res. 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

Identity or identical means amino acid sequence (or nucleic acid sequence) similarity and has an art recognized meaning Sequences with identity share identical or similar amino acids (or nucleic acids). Sequence identity is the percentage of amino acids identical to those in the antibody's original amino acid sequence, determined after the sequences are aligned and gaps are appropriately introduced to maximize the sequence identity as necessary. Thus, a candidate sequence sharing 85% amino acid sequence identity with a reference sequence requires that, following alignment of the candidate sequence with the reference sequence, 85% of the amino acids in the candidate sequence are identical to the corresponding amino acids in the reference sequence, and/or constitute conservative amino acid changes.

Antibodies of the invention can comprise CDRs of 6C8, 4F1, 14A12, or 18D3 antibodies or variant antibodies comprising one or more variant CDRs. These variant antibodies can have an activity equivalent (e.g., binding to canine CD20 with the same or substantially similar $K_d$ as an antibody produced by a hybridoma of Table 1) to that of 6C8, 4F1, 14A12, or 18D3. Antibody variants retain substantially the same functional activity of 6C8, 4F1, 14A12, or 18D3 antibodies. Naturally occurring functionally active variant antibodies such as allelic variants and species variants and non-naturally occurring functionally active variants are included in the invention and can be produced by, for example, mutagenesis techniques or by direct synthesis. Antibody variants are encoded by variant polypeptides and variant CDRs of SEQ ID NOs:1-32.

The invention also includes polypeptide variants or CDR variants of SEQ ID NOs:1-32. Polypeptide variants or CDR variant of SEQ ID NOs:1-36 can comprise one or more amino acid substitutions, additions or deletions. In one embodiment, a variant polypeptide or variant CDR includes an amino acid sequence at least about 75% identical to a sequence shown as SEQ ID NOs:1-36. Preferably, the variant polypeptide or CDR is at least about 75%, 80%, 85%, 90%, 95%, 98%, 99% or more identical to SEQ ID NOs:1-36. Variant polypeptides or variant CDRs encode a variant antibody, which is an antibody comprising an amino acid sequence of SEQ ID NOs:1-32 in which one or more amino acid residues have been added, substituted or deleted. For example, the variable region of an antibody can be modified to improve its biological properties, such as antigen binding. Such modifications can be achieved by e.g., site-directed mutagenesis, PCR-based mutagenesis, cassette mutagenesis. Variant antibodies comprise an amino acid sequence which is at least about 75%, 80%, 85%, 90%, 95%, 98%, 99% or more identical to the amino acid sequence of a heavy or light chain variable region of 6C8, 4F1, 14A12, 18D3. In one embodiment of the invention, a variant antibody retains the same function of a 6C8, 4F1, 14A12, 18D3 antibody (e.g., binds canine CD20 (in particular an extracellular region of canine CD20) at the same or substantially similar $K_d$ as an antibody produced by the hybridomas shown in Table 1, e.g. within about 1, 2, 3, 4, 5, 6, 7, 8, 9, 10, 15, or 20% of the IQ of an antibody produced by the hybridomas shown in Table 1). In another embodiment of the invention, a variant antibody may have a function that is somewhat altered from a 6C8, 4F1, 14A12, 18D3 antibody (e.g., binding canine CD20 with a $K_d$ that is higher or lower than an 6C8, 4F1, 14A12, 18D3 antibody).

Polypeptide sequences can be modified, for example, by synthesizing multiple polynucleotides encoding the amino acid sequence of a variant variable region, and preparing nucleic acids encoding the variable region by PCR using the polynucleotides. Antibodies that comprise one or more CDRs can be prepared by inserting the polynucleotide into an appropriate expression vector and expressing the polynucleotide. For example, the polynucleotides are synthesized using mixed nucleotides to prepare a DNA library that encodes a variety of antibodies comprising CDRs with various amino acids introduced at certain positions. An antibody can be isolated by selecting from the library a clone encoding an antibody that binds to canine CD20 with a $K_d$ that is the same or substantially similar to the $K_d$ of an antibody produced by a hybridoma shown in Table 1.

A polypeptide of the invention can be covalently or non-covalently linked to an amino acid sequence to which the polypeptide is not normally associated with in nature. Additionally, a polypeptide of the invention can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. A fusion protein is two or more different amino acid sequences operably linked to each other. A fusion protein construct can be synthesized chemically using organic compound synthesis techniques by joining individual polypeptide fragments together in fixed sequence. A fusion protein construct can also be expressed by a genetically modified host cell (such as E. coli) cultured in vitro, which carries an introduced expression vector bearing specified recombinant DNA sequences encoding the amino acids residues in proper sequence. The heterologous polypeptide can be fused, for example, to the N-terminus or C-terminus of a polypeptide of the invention. A polypeptide of the invention can also comprise homologous amino acid sequences, i.e., other CD20 or CD20-derived sequences. More than one polypeptide of the invention can be present in a fusion protein. Fragments of polypeptides of the invention can be present in a fusion protein of the invention. A fusion protein of the invention can comprise, e.g., one or more of SEQ ID NOs:1-36, fragments thereof, or combinations thereof. Polypeptides of the invention can be in a multimeric form. That is, a polypeptide can comprise one or more copies of SEQ ID NOs:1-36 or a combination thereof.

In one embodiment of the invention, a polypeptide of the invention is derived from a canine A polypeptide of the invention can be isolated from cells or tissue sources using standard protein purification techniques. Polypeptides of the invention can also be synthesized chemically or produced by recombinant DNA techniques. For example, a polypeptide of the invention can be synthesized using conventional peptide synthesizers.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system.

Antibodies

Antibodies refer to an intact antibody or an antigen-binding fragment thereof that competes with the intact antibody for antigen binding. Antigen-binding fragments can be produced by recombinant DNA techniques or by enzymatic or chemical cleavage of intact antibodies. Antigen-binding fragments include an antigen-binding domain or a variable region and include, e.g., Fab, Fab', F(ab')$_2$, Fab'-SH, Fab-like antibodies (an antigen-binding fragment containing variable regions of a heavy chain and light chain that is equivalent to Fab fragments that are obtained by papain digestion), F(ab')$_2$-like antibodies (an antigen-binding fragment containing two antigen-binding domains that is equivalent to F(ab')$_2$ fragments that are obtained by pepsin digestion), Fv, linear antibodies, multispecific antibodies prepared from antibody fragments, and single-chain antibodies (scFv). An antibody can be a monoclonal antibody, polyclonal antibody, diabody, bispecific antibody, multifunctional antibody, chimeric antibody, caninized antibody, canine antibody, humanized antibody, human antibody, synthetic antibody, or CDR-grafted antibody. An antibody of the invention can be any isotype including IgG (IgG1, IgG2, IgG2a, Ig2b, IgG3, IgG4), IgM, IgA (IgA1 and IgA2), IgD, and IgE.

An epitope is any protein determinant that specifically binds to an immunoglobulin or T-cell receptor. Epitopes can comprise chemically active surface groupings of molecules such as amino acids or sugar side chains and can have specific three dimensional structural characteristics, as well as specific charge characteristics.

An antibody of the invention binds to an epitope that overlaps with or is the same (i.e., a substantially identical epitope) as any of the monoclonal antibodies shown in Table 1. An antibody that binds to an epitope substantially identical to an epitope of canine CD20 to which a monoclonal antibody of Table 1 binds, can be obtained by analyzing epitopes of the monoclonal antibodies of Table 1 using well known epitope mapping methods. Competitive assays can be used to determine if two antibodies bind to a substantially identical epitope of a canine CD20. Where the binding of a first anti-canine CD20 antibody with canine CD20 is competitively inhibited by a second anti-canine CD20 antibody, the first antibody and the second antibody can be considered to bind to a substantially identical epitope on canine CD20. Competitively inhibits means that an antibody or antigen-binding fragment thereof can specifically bind an epitope that a monoclonal antibody produced by a hybridoma cell line shown in Table 1 is directed to, using conventional reciprocal antibody competition assays. See e.g., Belanger et al. (1973), Clinica Chimica Acta 48:15. Therefore, the invention comprises antibodies that bind to an epitope that is substantially identical to or the same as an epitope of canine CD20 to which an antibody produced by a hybridoma of Table 1 binds, and that can also comprise the activity of inducing apoptosis of CD20+ cells and/or binding to canine lymphocytes.

Antibodies that competitively inhibit binding of one or more of 4F1, 6C8, 14A12, 18D3 or antigen binding fragments thereof, reduce the binding of one or more of 4F1, 6C8, 14A12, 18D3 or antigen binding fragments thereof to a canine CD20 polypeptide, CD20+ cells, and/or canine lymphocytes by about 30%, 50%, 75%, 90% or 100% in a competitive inhibition assay.

In one embodiment of the invention, an antibody or an antigen-binding fragment thereof specifically binds the extracellular domain 2 of a canine polypeptide comprising the amino acid sequence of SEQ ID NO:33.

In another embodiment of the invention, an antibody or an antigen-binding fragment thereof specifically binds a polypeptide comprising the amino acid sequence of SEQ ID NO:35 or SEQ ID NO:36.

In yet another embodiment of the invention, an antibody or an antigen-binding fragment thereof specifically binds a polypeptide comprising the amino acid sequence of SEQ ID NO:33 and SEQ ID NO:35.

In an additional embodiment of the invention, an antibody or an antigen-binding fragment thereof specifically binds a polypeptide comprising the amino acid sequence of SEQ ID NO:33 and SEQ ID NO:36.

Antibodies of the invention, fragments thereof, or variants thereof can specifically bind canine CD20 with a wide range of disassociation constants ($K_d$). For example, an antibody can bind canine CD20 with a $K_d$ equal to or less than about $10^{-7}$ M, such as but not limited to, $0.1$-$9.9 \times 10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$ or any range or value therein, as determined by e.g, surface plasmon resonance or the Kinexa method. The invention encompasses antibodies that bind canine CD20 polypeptides with a disassociation constant or $K_d$ that is within any one of the ranges that are between each of the individual recited values. An antibody has the same or substantially identical activity as antibodies produced by the hybridomas shown in Table 1 when the $K_d$ for binding to canine CD20 (in particular an extracellular portion of canine CD20) is within about 0.1., 0.2, 0.3, 0.4, 0.5, 1, 2, 3, 4, 5, 6, 7, 8, 9, 10, 15, or 20% (or any range or particular value between 0.1 and 20%) of the $K_d$ for binding to canine CD20 (in particular an extracellular portion of canine CD20) of an antibody produced by the hybridomas shown in Table 1.

Antibodies of the invention, fragments thereof or variants thereof can bind canine CD20 polypeptides with an off rate ($K_{off}$) of less than or equal to 01.-9.9×10$^{-3}$ sec$^{-1}$, 10$^{-4}$ sec$^{-1}$, 10$^{-5}$ sec$^{-1}$, 10$^{-6}$ sec$^{-1}$, 10$^{-7}$ sec$^{-1}$. The invention encompasses antibodies that bind canine CD20 polypeptides with an off rate that is within any one of the ranges that are between each of the individual recited values. An antibody has the same or substantially identical activity as antibodies produced by the hybridomas shown in Table 1 when the $K_{off}$ for binding to canine CD20 (in particular an extracellular portion of canine CD20) is within about 0.1., 0.2, 0.3, 0.4, 0.5, 1, 2, 3, 4, 5, 6, 7, 8, 9, 10, 15, or 20% (or any range or particular value between 0.1 and 20%) of the $K_{off}$ for binding to canine CD20 (in particular an extracellular portion of canine CD20) of an antibody produced by the hybridomas shown in Table 1.

Antibodies of the invention, fragments thereof, or variants thereof can bind canine CD20 polypeptides, CD20$^+$ cells, and/or canine lymphocytes with an on rate ($K_{on}$) greater than or equal to 0.1-9.9×10$^3$ M$^{-1}$ sec$^{-1}$, 10$^4$ M$^{-1}$ sec$^{-1}$, 10$^5$ M$^{-1}$ sec$^{-1}$, 10$^6$ M$^{-1}$ sec$^{-1}$, 10$^7$ M$^{-1}$ sec$^{-1}$, 10$^8$ M$^{-1}$ sec$^{-1}$. The invention encompasses antibodies that bind canine CD20 polypeptides with on rate that is within any one of the ranges that are between each of the individual recited values. An antibody has the same or substantially identical activity as antibodies produced by the hybridomas shown in Table 1 when the $K_{on}$ for binding to canine CD20 (in particular an extracellular portion of canine CD20) is within about 0.1, 0.2, 0.3, 0.4, 0.5, 1, 2, 3, 4, 5, 6, 7, 8, 9, 10, 15, or 20% (or any range or particular value between 0.1 and 20%) of the $K_{on}$ for binding to canine CD20 (in particular an extracellular portion of canine CD20) of an antibody produced by the hybridomas shown in Table 1.

Antibodies of the invention specifically bind canine CD20. In this context "specifically binds" means that the antibody recognizes and binds to canine CD20 with greater affinity than to other, non-specific molecules that are not canine CD20. For example, an antibody raised against an antigen (polypeptide) to which it binds more efficiently than to a non-specific antigen (e.g., a canine protein that is not related to or homologous to CD20) can be described as specifically binding to the antigen. Binding specificity can be tested using, for example, an enzyme-linked immunosorbant assay (ELISA), a radioimmunoassay (RIA), or a western blot assay using methodology well known in the art.

The invention also encompasses antibodies, fragments thereof, or variants thereof that have one or more of the same or substantially similar biological characteristics as the antibodies shown in Table 1. Biological characteristics are the in vitro or in vivo activities or properties of the antibodies shown in Table 1, including, for example, the ability to bind to canine CD20 (in particular, extracellular region 2) with a substantially similar $K_d$, $K_{off}$, and/or $K_{on}$ rate and/or cause apoptosis of CD20$^+$ cells and/or bind canine lymphocytes.

Antibodies of the invention can be produced using methods known to those of skill in the art. For example, a canine CD20 antigen or a fragment thereof can be used to immunize animals. The CD20 or fragment thereof can be conjugated to a carrier protein and/or administered to the animals with an adjuvant. A canine CD20 antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, canine CD20 can be isolated and screened. A series of short peptides, which together span the entire CD20 polypeptide sequence, can be prepared by proteolytic cleavage. By starting with, for example, 100-mer polypeptide fragments, each fragment can be tested for the presence of epitopes recognized in an ELISA. For example, in an ELISA assay a canine CD20 antigen, such as a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

A monoclonal antibody is an antibody obtained from a group of substantially homogeneous antibodies. A group of substantially homogeneous antibodies can contain a small amount of naturally occurring mutants. Monoclonal antibodies are highly specific and interact with a single antigenic site. Each monoclonal antibody typically targets a single epitope while polyclonal antibody populations typically contain various antibodies that target a group of diverse epitopes. Monoclonal antibodies can be produced by many methods including, for example, hybridoma methods (Kohler and Milstein, Nature 256:495, 1975), recombination methods (U.S. Pat. No. 4,816,567), isolation from phage antibody libraries (Clackson et al., Nature 352:624-628, 1991; Marks et al., J. Mol. Biol. 222:581-597, 1991).

Methods for preparing monoclonal antibodies from hybridomas are well known to those of skill in the art and include, e.g., standard cell culture methods and ascites production methods. Recombinant antibodies produced by gene engineering can be made using the polynucleotide sequences of the invention. Genes encoding antibodies or fragments thereof can be isolated from hybridomas of the invention or other hybridomas. The genes can be inserted into an appropriate vector and introduced into a host cell. See, e.g., Borrebaeck & Larrick, Therapeutic Monoclonal Antibodies, Macmillan Publ. Ltd, 1990.

Whole antibodies can also be made using PCR primers having VH or VL nucleotide sequences, a restriction site, and a flanking sequence to protect the restriction site to amplify the VH or VL sequences in scFv clones. Using well known cloning techniques, the PCR amplified VH domains can be cloned into vectors expressing a VH constant region, e.g., a canine constant region, and the PCR amplified VL domains can be cloned into vectors expressing a VL constant region, e.g., canine kappa or lambda constant regions. The vectors for expressing the VH or VL domains can comprise, e.g., a promoter suitable to direct expression of the heavy and light chains in the chosen expression system, a secretion signal, a cloning site for the immunoglobulin variable domain, immunoglobulin constant domains, and a selection marker. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

Chimeric antibodies have a part of a heavy chain and/or light chain that is derived from a specific species or a specific antibody class or subclass, and the remaining portion of the chain is derived from another species, or another antibody class or subclass. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397. Chimeric antibodies can be produced using a variety of techniques including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28:489-498 (1991); Studnicka et al., Protein Engineering 7(6):805-814 (1994); Roguska et al., PNAS 96:969-973 (1994)), and chain shuffling (U.S. Pat. No. 5,565,332).

In one embodiment, a chimeric antibody can comprise variable and constant regions of species that are different from each other, for example, an antibody can comprise the heavy chain and light chain variable regions of a non-human mammal such as a mouse, and the heavy chain and light chain constant regions of a canine Such an antibody can be obtained by ligating a polynucleotide encoding a variable region of a mouse antibody to a polynucleotide encoding a constant region of a canine antibody; incorporating the ligated polynucleotides into an expression vector; and introducing the vector into a host cell for production of the antibody. See WO 96/02576. The host cells can be eukaryotic cells, such as mammalian cells, including, e.g., CHO cells, lymphocytes, and myeloma cells. The chimeric antibody can comprise additional amino acid acids that are not included in the CDRs introduced into the recipient antibody, nor in the framework sequences. These amino acids can be introduced to more accurately optimize the antibody's ability to recognize and bind to an antigen. For example, as necessary, amino acids in the framework region of an antibody variable region can be substituted such that the CDR of a reshaped canine antibody forms an appropriate antigen-binding site. See Sato et al., Cancer Res. (1993) 53:851-856.

The nucleic acid sequences for four different canine Ig gamma constant regions have been cloned and sequenced. See Tang et al., Vet. Immunol. Immunopath. (2001) 80:259. The sequences for canine lambda and kappa chain constant regions, along with gamma constant regains have been reported in U.S. Pat. No. 5,593,861.

Human antibodies can be made by sensitizing human lymphocytes with antigens of interest or cells expressing antigens of interest in vitro; and fusing the sensitized lymphocytes with human myeloma cells. Alternatively, a human antibody can be made by using an antigen to immunize a transgenic animal that comprises a partial or entire repertoire of human antibody genes. See Green et al., Nature Genetics 7:13-21 (1994); Mandez et al., Nature Genetics 15:146-156 (1997); Lonberg et al., Nature 368:856-859 (1994); WO 93/12227; WO 92/03918; WO 94/02602, WO 94/25585, WO 96/34096, and WO 96/33735).

Human antibodies can also be made by panning with a human antibody library. For example, the variable region of a human antibody is expressed as a single chain antibody (scFv) on the surface of a phage, using phage display method, and phages that bind to the antigen are selected. By analyzing the polynucleotides of selected phages, the polynucleotides encoding the variable regions of human antibodies that bind to the antigen can be determined. If the polynucleotide sequences of scFvs that bind to the antigen are identified, appropriate expression vectors comprising these sequences can be constructed, and then introduced into appropriate hosts and expressed to obtain human antibodies. See WO 92/01047, WO 92/20791, WO 93/06213, WO 93/11236, WO 93/19172, WO 95/01438, and WO 95/15388. These same human antibody production methods can be used to make canine antibodies.

Antibodies of the invention can be used to generate anti-idiotype antibodies that "mimic" canine CD20 polypeptides using techniques well known to those skilled in the art. See, Greenspan & Bona, FASEB 17:437-444 (1993); Nissinoff, J. Immunol. 147:2429-2438 (1991).

Antibodies can be purified by any method, including, e.g., protein A-Sepharose methods, hydroxyapatite chromatography, salting-out methods with sulfate, ion exchange chromatography, affinity chromatography, filtration, unitrafiltration, dialysis, preparative polyacrylamide gel electrophoresis, isoelectrofocusing or combinations thereof.

Antibodies of the invention can be covalently attached to other molecules such that covalent attachment does not affect the ability of the antibody to bind to canine CD20. For example, antibodies can be modified by, e.g., glycosylation, acetylation, pegylation, phosphorylation, amidation, derivatization by known protecting/blocking groups, proteolytic cleavage, linkage to a cellular ligand or other protein, etc. Additionally, an antibody can contain one or more non-standard amino acids.

One embodiment of the invention provides mixtures of antibodies, antigen-binding fragments thereof, or variants thereof that bind to canine CD20, wherein the mixture has at least two, three, four, five or more different antibodies of the invention.

The invention also provides for panels of antibodies that have different affinities for canine CD20, different specificities for canine CD20, or different dissociation rates. The invention provides panels of at least about 4, 5, 10, 20, 50, 100, 250, 500, 750, or 1,000 antibodies.

Polynucleotides

Polynucleotides of the invention contain less than an entire canine genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% pure by dry weight. Purity can be measured by a method such as column chromatography, polyacrylamide gel electrophoresis, or HPLC analysis. The polynucleotides of the invention encode the polypeptides described above. In one embodiment of the invention the polynucleotides encode polypeptides shown in, e.g., SEQ ID NOs:1-36 or portions or combinations thereof.

The polynucleotides of the invention encode the polypeptides of the invention described above, as well as fragments thereof. A polynucleotide fragment can be about 9, 18, 21, 27, 30, 33, 39, 48, 51, 75, 100, 120, 130, 140, 150 or more polynucleotides. One of skill in the art can obtain the polynucleotide sequences of the invention using the disclosed polypeptide sequences and codon tables. Polynucleotides can contain naturally occurring polynucleotides or sequences that differ from those of any naturally occurring sequences or polynucleotides. Polynucleotides of the invention can differ from naturally occurring nucleic acids, but still encode naturally occurring amino acids due to the degeneracy of the genetic code. Polynucleotides of the invention can also comprise other heterologous nucleotide sequences, such as sequences coding for linkers, signal sequences, amino acid spacers, heterologous signal sequences, TMR stop transfer sequences, transmembrane domains, or ligands useful in protein purification such as glutathione-S-transferase, histidine tag, and staphylococcal protein A. Polynucleotides of the invention can also comprise other nucleotide sequences, e.g., other CD20 or CD20-derived sequences.

Methods for introducing polynucleotides of the invention (e.g., vectors comprising the polynucleotides or naked polynucleotides) into cells, either transiently or stably, are well known in the art. For example, transformation methods using standard $CaCl_2$, $MgCl_2$, or RbCl methods, protoplast fusion methods or transfection of naked or encapsulated nucleic acids using calcium phosphate precipitation, microinjection, viral infection, and electroporation.

In one embodiment of the invention, a polynucleotide of the invention is derived from a mammal, such as a dog. Polynucleotides can also be synthesized in the laboratory, for example, using an automatic synthesizer. An amplification method such as PCR can be used to amplify polynucleotides from either genomic DNA or cDNA encoding the polypeptides. Polynucleotide molecules encoding a variant polypeptide can also be isolated by a gene amplification method such as PCR using a portion of a nucleic acid molecule DNA encoding a polypeptide shown in SEQ ID NOs:1-36 as the probe.

Polynucleotides and fragments thereof of the invention can be used, for example, as probes or primers to detect the presence of canine CD20 polynucleotides in a sample, such as a biological sample. A biological sample can be, e.g., lymph node or tissue aspirate, serum, lymphocytes, whole blood, cellular suspension, or fluid effusion. The ability of such probes to specifically hybridize to polynucleotide sequences will enable them to be of use in detecting the presence of complementary sequences in a given sample. Polynucleotide probes of the invention can hybridize to complementary sequences in a sample such as a biological sample, for example, lymph tissue. Polynucleotides from the sample can be, for example, subjected to gel electrophoresis or other size separation techniques or can be dot blotted without size separation. The polynucleotide probes are preferably labeled. Suitable labels, and methods for labeling probes are known in the art, and include, for example, radioactive labels incorporated by nick translation or by kinase, biotin, fluorescent probes, and chemiluminescent probes. The polynucleotides from the sample are then treated with the probe under hybridization conditions of suitable stringencies.

The stringency of hybridization conditions for a polynucleotide encoding a variant polypeptide of the invention to a polynucleotide encoding polypeptides shown in SEQ ID NOs:1-36 can be, for example, 10% formamide, 5× SSPE, 1× Denhart's solution, and 1× salmon sperm DNA (low stringency conditions). More preferable conditions are, 25% formamide, 5× SSPE, 1× Denhart's solution, and 1× salmon sperm DNA (moderate stringency conditions), and even more preferable conditions are, 50% formamide, 5× SSPE, 1× Denhart's solution, and 1× salmon sperm DNA (high stringency conditions). However, several factors influence the stringency of hybridization other than the above-described formamide concentration, and one skilled in the art can suitably select these factors to accomplish a similar stringency. See e.g., Ausubel (ed.), Current Protocols in Molecular Biology, John Wiley and Sons, Inc. (1994); Maniatis et al., Molecular Cloning: A Laboratory Manual, Cold Spring Harbor laboratory, Cold Spring Harbor, N.Y. (1989)). That is, a polynucleotide encoding a variant polypeptide of the invention will hybridize to a polynucleotide encoding SEQ ID NOs:1-36 under low or high or both stringency conditions.

An isolated polynucleotide is a nucleic acid molecule that is not immediately contiguous with one or both of the 5' and 3' flanking sequences with which it is normally contiguous when present in a naturally occurring genome. Therefore, an isolated polynucleotide can be, for example, a polynucleotide that is incorporated into a vector, such as a plasmid or viral vector, a polynucleotide that is incorporated into the genome of a heterologous cell (or the genome of a homologous cell, but at a site different from that where it naturally occurs); and a polynucleotide that exists as a separate molecule such as a polynucleotide produced by PCR amplification, chemically synthesis, restriction enzyme digestion, or in vitro transcription. An isolated polynucleotide is also a nucleic acid molecule, such as a recombinant nucleic acid molecule that forms part of hybrid polynucleotide encoding additional polypeptide sequences that can be used for example, in the production of a fusion protein.

A polynucleotide can also comprise one or more expression control sequences such as promoters or enhancers, for example. A polynucleotide of the invention can be present in a vector, such as, for example, an expression vector. If desired, polynucleotides can be cloned into an expression vector comprising, for example, promoters, enhancers, or other expression control sequences that drive expression of the polynucleotides of the invention in host cells. The polynucleotides can be operably linked to the expression control sequences.

Vectors and Host Cells

A polypeptide can be expressed in systems, e.g., cultured cells, which result in substantially the same post-translational modifications present as when the polypeptide is expressed in a native cell, or in systems that result in the alteration or omission of post-translational modifications, e.g., glycosylation or cleavage, present when expressed in a native cell.

An expression vector can be, for example, a plasmid, such as pBR322, pUC, or Co1E1, or an adenovirus vector, such as an adenovirus Type 2 vector or Type 5 vector. Vectors suitable for use in the present invention include, for example, bacterial vectors, mammalian vectors, viral vectors (such as retroviral, adenoviral, adeno-associated viral, herpes virus, simian virus 40 (SV40), and bovine papilloma virus vectors) and baculovirus-derived vectors for use in insect cells. Polynucleotides in such vectors are preferably operably linked to a promoter, which is selected based on, e.g., the cell type in which expression is sought.

The expression vector can be transferred to a host cell by conventional techniques and the transfected cells are then cultured by conventional techniques to produce an antibody of the invention. The invention includes host cells containing polynucleotides encoding an antibody of the invention (e.g., whole antibody, a heavy or light chain thereof, or portion thereof, or a single chain antibody of the invention, or a fragment or variant thereof), operably linked to a heterologous promoter. For the expression of entire antibody molecules, vectors encoding both the heavy and light chains may be co-expressed in the host cell for expression of the entire immunoglobulin molecule.

Host cells into which vectors, such as expression vectors, comprising polynucleotides of the invention can be introduced include, for example, prokaryotic cells (e.g., bacterial cells) and eukaryotic cells (e.g., yeast cells; fungal cells; plant cells; insect cells; and mammalian cells). Such host cells are available from a number of different sources that are known to those skilled in the art, e.g., the American Type Culture Collection (ATCC), Manassas, Va. Host cells into which the polynucleotides of the invention have been introduced, as well as their progeny, even if not identical to the parental cells, due to mutations, are included in the invention. Host cells can be transformed with the expression vectors to express the antibodies or antigen-binding fragments thereof. Host cells expressing antibodies or antigen-binding fragments thereof of the present invention include cells and hybridomas transformed with a polynucleotide of the invention.

One embodiment of the invention provides methods of producing a recombinant cell that expresses a canine CD20 antibody, antigen-binding fragment thereof or portion thereof, comprising transfecting a cell with a vector comprising a polynucleotide of the invention. A canine CD20 antibody, or fragment, or portion thereof, can then be produced by expressing the polypeptide in the recombinant host cell.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

Methods of Treatment

Antibodies of the invention can used to treat, ameliorate, or prevent canine CD20+ B-cell lymphoma, immune-mediated hemolytic anemia, immune-mediated thrombocytopenia, and systemic lupus erythematosus (SLE) or other disease or disorder associated with aberrant CD20 or B-cell expression (e.g., over-expression of B cells or CD20 or dysfunctional B cells).

The invention also encompasses multimodal therapeutic methods wherein anti-CD20 antibody administration is supplemented with chemotherapy, radiation therapy, hormonal therapy, immunotherapy, anti-angiogenesis agents, anti-inflammatory agents or therapeutic proteins, such as immunoconjugates and antibody fusion proteins. Combinations can be administered either concomitantly, e.g., as an admixture; separately but simultaneously or concurrently; or sequentially. This includes presentations where the combined agents are administered together as a therapeutic mixture, and also procedures where the combined agents are administered separately but simultaneously, e.g., as through separate intravenous lines into the same individual. Administration "in combination" further includes the separate administration of one of the compounds or agents given first, followed by the second.

In general, the dosage of administered anti-CD20 antibodies, anti-CD20 antibody components, will vary depending upon such factors as the canine's age, weight, sex, general medical condition and previous medical history. Typically, it is desirable to provide the recipient with a dosage of antibody that is in the range of from about 1 pg/kg to 1,000 mg/kg (or any range between 1 pg/kg to 1,000 mg/kg) (amount of agent/body weight of canine), although a lower or higher dosage also may be administered as circumstances dictate. Other mammals can be treated with anti-CD20 antibodies of the invention including, for examples, cats and ferrets.

Administration of antibodies and antibody components to a patient can be orally or parenterally. For example, compositions of the invention can be delivered by injection, nasal formulation, pulmonary formulation, and cutaneous formulation. Injections can be delivered systemically or locally, intravenously, intraarterially, intraperitoneally, intramuscularly, subcutaneously, intrapleurally, intrathecally, by perfusion through a regional catheter, or by direct intralesional injection. When administering antibodies by injection, the administration can be by continuous infusion or by single or multiple boluses.

Compositions of the invention can comprise anti-CD20 antibodies and a pharmaceutically acceptable buffer, for example, sterile saline, sterile buffered water, propylene glycol. Methods for preparing administrable agents, such as parenterally administrable agents, are described in Pharmaceutical Carriers & Formulations, Martin, Remington's Pharmaceutical Sciences, 15th Ed. (Mack Pub. Co., Easton, Pa. 1975). An antibody formulation of the invention can comprise pharmaceutically acceptable carriers and/or additives. For example, carriers can include, without limitation, surfactants, excipients, antioxidants, coloring agents, flavoring agents, preservatives, stabilizers, buffering agents, chelating agents, suspending agents, isotonizing agents, binders, disintegrators, lubricants, fluidity promoters, and corrigents. Antibody formulations can also comprise proteins such as serum albumin, gelatin, and immunoglobulin, and amino acids such as glycine, glutamine, asparagine, arginine, and lysine. Aqueous antibody formulations can comprise an isotonic solution comprising, for example, physiological saline, dextrose, and other adjuvants, including, for example, D-sorbitol, D-mannose, D-mannitol, and sodium chloride, which can also contain solubilizing agents and non-ionic detergents.

Antibody formulations can be encapsulated in microcapsules made of, e.g., hydroxycellulose, gelatin, polymethylmethacrylate, and made into components of colloidal drug delivery systems (liposomes, albumin microspheres, microemulsions, nano-particles, and nano-capsules). See Remington's Pharmaceutical Science 16th edition, Oslo Ed. (1980)).

Polynucleotides encoding antibodies can be used for gene therapy. Gene therapy is therapy performed by the administration to a subject of an expressed or expressible polynucleotide. Polynucleotides produce their encoded protein that mediates a therapeutic effect. See Goldspiel et al., Clinical Pharmacy 12:488-505 (1993); Wu & Wu, Biotherapy 3:87-95 (1991); Tolstoshev, Ann. Rev. Pharmacol. Toxicol. 32:573-596 (1993); Mulligan, Science 260:926-932 (1993); and Morgan & Anderson, Ann. Rev. Biochem. 62:191-217 (1993); May, TIBTECH 11(5):155-215 (1993).

A composition for gene therapy can comprise polynucleotides encoding an antibody or antigen-binding fragment thereof. The polynucleotides can be present in an expression vector that expresses the antibody or fragments thereof in a suitable host. The polynucleotides can include enhancers and/or promoters, such as heterologous promoters, that are operably linked to an antibody coding region. The promoter can be inducible, constitutive, and/or tissue-specific. Polynucleotides can be used wherein the antibody coding sequences and any other desired sequences are flanked by regions that promote homologous recombination at a desired site in the genome, thus providing for intrachromosomal expression of the antibody encoding polynucleotides. See Koller & Smithies, Proc. Natl. Acad. Sci. USA 86:8932-8935 (1989); Zijlstra et al., Nature 342:435-438 (1989).

Delivery of the polynucleotides into a subject can be direct, wherein the subject is directly exposed to the polynucleotide or expression vectors, or indirect, wherein cells are first transformed with the polynucleotides in vitro, then transplanted into the subject.

Polynucleotides of the invention can be directly administered in vivo, where they are expressed to produce antibodies or fragments thereof. Direct administration includes, e.g., infection using defective or attenuated retroviruses or other viral vectors (see U.S. Pat. No. 4,980,286), by direct injection of naked DNA, by use of microparticle bombardment (e.g., a gene gun; Biolistic, Dupont), coating the polynucleotides with lipids or cell-surface receptors or transfecting agents, encapsulation in liposomes, microparticles, or microcapsules, or by administering the polynucleotides linked to a peptide that is known to enter the nucleus by e.g., administering the polynucleotides linked to a ligand that can undergo receptor mediated endocytosis. See Wu & Wu, J. Biol. Chem. 262:4429-4432 (1987). In another embodiment, polynucleotide-ligand complexes can be formed where the ligand comprises a fusogenic viral peptide to disrupt endosomes, allowing the polynucleotide to avoid lysosomal degradation. Polynucleotides can also be targeted in vivo for cell specific uptake and expression by targeting the polynucleotides to a specific receptor. See PCT Publications WO 92/06180; WO 92/22635; WO92/20316; WO93/14188; WO 93/20221).

Compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Peptides Derived from Canine CD20

The predicted structure of canine CD20 is that of a type III 4-span membrane protein, having two extracellular domains. Extracellular domain 1 encompasses approximately 5 amino acids, and extracellular domain 2 encompasses approximately 50 amino acids. A polypeptide sequence was identified that represents the predominant extracellular domain (ED) 2 of the canine CD20 protein. This ED peptide was synthesized alone:
SEQ ID NO:33
DIFNITISHFLKMENLN-
LIKAPIPYVDIHNCDPANPSEKNSLSIQYCGSIRSV
and in conjunction with a murine T-cell epitope from ovalbumin:
SEQ ID NO:34
DDLQAVHAAHAEINEADHIDIDDIFNIT-
ISHFLKMENLNLIKAPIPYVDIHNCDPANPSEK NSL-
SIQYCGSIRSV. The latter peptide was conjugated to KLH and used to immunize mice with the intention of generating monoclonal antibodies to the extracellular domain 2 of canine CD20.

CD20 ELISA for Hybridoma Screening

A polypeptide ELISA was performed by dissolving 1 mg of ED peptide (SEQ ID NO:33) in 1 ml of DMSO (Sigma). Polypeptides were coated onto 96-well microtiter plates (Immunlon 4HB, Dynatech) at a concentration of 10 ug/ml in 50 mM carbonate (pH 9) overnight at room temperature. Plates were washed four times in PBS-T (phosphate buffered saline (pH 7.2), 0.05% TWEEN® 20 (polysorbate)) and blocked with 2% TWEEN® 20 (polysorbate) in 100 mM Tris (pH7.4) for 2 hours at room temperature. Plates were washed four times in PBS-T before hybridoma supernatants or purified antibody was added. Plates were incubated for 1 hour at room temperature, washed four times in PBS-T, and a 1:2500 dilution of goat anti-mouse HRPO (Jackson ImmunoResearch) in sample diluent (50 mM Tris (pH 7.2), 0.05% TWEEN® 20 (polysorbate), 50% fetal bovine serum (FBS)) was added. Following an one hour incubation at room temperature, plates were washed six times in PBS-T and developed with a TMB substrate.

Fusion and Hybridoma Screening

Standard fusion protocols were followed to generate initial hybridomas. An anti-mouse conjugate specific for the Fc portion of murine IgG was used to identify positive clones on CD20-peptide coated ELISA plates. Positive clones were propagated using a modified limiting dilution technique. Because the hybridomas were initially difficult to culture when plated at a very low number of cells per well, the subcloning was performed gradually, and with time the cells demonstrated stability and consistent proliferation. Hybridoma supernatant was tested to determine isotype using a commercially available kit (Roche Applied Sciences). Table 1 lists the 4 IgG hybridomas and their isotype.

TABLE 1

| Antibody | Isotype |
| --- | --- |
| 6C8 | IgG1 |
| 4F1 | IgG3 |
| 14A12 | IgG2b |
| 18D3 | IgG2b |

The hybridomas were deposited on Aug. 27, 2008, under the Budapest Treaty at American Type Culture Collection, 10801 University Blvd. Manassas Va., 20110, as follows: 4F1: PTA-9433; 6C8: PTA-9434; 14A12: PTA-9435; 18D3: PTA-9436. The variable heavy and variable light chains were cloned and sequenced for each monoclonal antibody.

Ascites Production

Figure 1B:
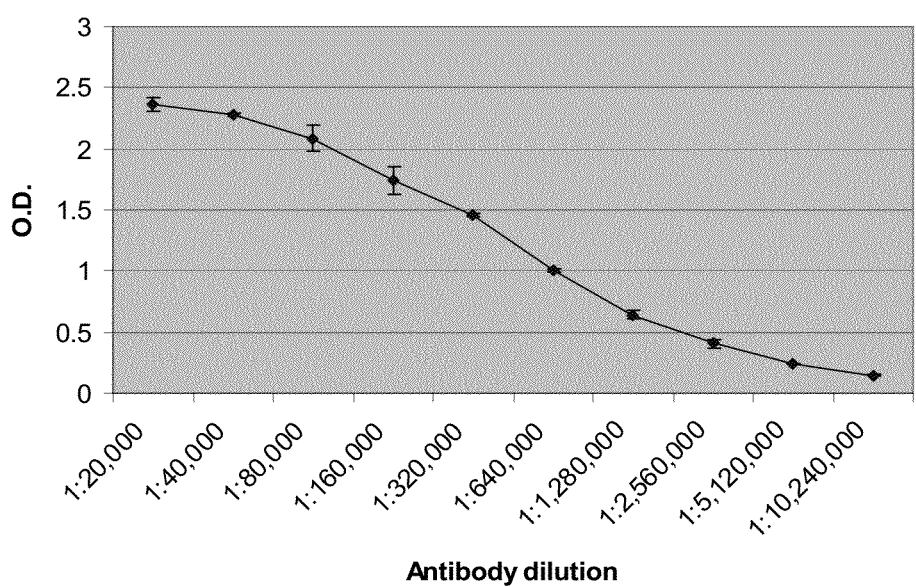

Four IgG secreting hybridomas were used to generate ascites according to standard methods. Following routine purification, the immunoglobulin was titered on the CD20-peptide ELISA (FIGS. 1A-B). Monoclonal antibody 6C8 has the greatest affinity for the canine CD20 extracellular domain 2 peptide (FIG. 1B).

Immunofluorescent Labeling of B-Cell Lymphoma:

Lymph node aspirates from a dog with a diagnosed B-cell lymphoma were labeled with hybridoma supernatant from 3 of the 4 cell lines. Each smear was outlined with an ImmEdge™ pen (Vector Labs), allowed to dry, and then fixed in acetone for 3 minutes. Following a 5 minute wash in PBS (pH 7.2), slides were treated with ammonium chloride (50 mM in PBS) for 15 minutes at room temperature. Following a 5 minute wash in PBS, slides were blocked in PBS/NGS (PBS with 15% normal goat serum) for 30 minutes at room temperature. Each hybridoma supernatant was then added to the slide and incubated for one hour at room temperature. Slides were washed twice for 5 minutes in PBS, followed by a 30 minute incubation in a 1:200 dilution of goat anti-mouse IgM+IgG (H+L) F(ab)₂ FITC (Jackson ImmunoResearch) in PBS/NGS. Following two 5 minute washes in PBS, slides were examined using fluorescent microscopy. All 3 of the clones tested showed immunofluorescent labeling of the canine B-cells, while monoclonal antibodies specific for the extracellular domain of human CD20 (1F5 (ATCC HB9645) and B1 (Biogenex)) did not label the canine B-cells.

Flow Cytometric Labeling of B-Cell Lymphoma

Fluorescent conjugates of all four IgG anti-canine CD20 monoclonal antibodies were made using a commercially available kit (Invitrogen, AF647 monoclonal antibody labeling kit, A20186). Antibody conjugates were used to label a lymph node aspirate from a dog diagnosed with B-cell lymphoma. $3.0 \times 10^6$ white blood cells were added to 3 ml of PBS/FBS (pH 7.2). and centrifuged at 900 g for 2 minutes (or 45 seconds in Drucker Model 642B centrifuge; 1600 g). The supernatant was removed with care to not disrupt the cell pellet. The cells were resuspended in 600 ul PBS/FBS. Two to six ul of each of the anti-canine CD20 AF647 antibody was placed into a separate plastic 12×75 tube. Isotype controls labeled with AF647 were used at a similar concentration in separate tubes. 100 ul of the cell suspension was placed into each tube. The cells were incubated for a minimum of 30 minutes in refrigerator and then diluted with 0.5-2.0 ml of PBS/FBS. Flow cytometry was performed on a Beckman Coulter Epics ELITE following routine procedures. All four monoclonal antibodies labeled the B-lymphocytes in the sample, with 6C8 having the brightest labeling of the four.

In order to confirm that antibodies specific for an extracellular domain of human CD20 do not cross react with canine lymphocytes several experiments were conducted. Both the 1F5 (ATCC HB9645) and B1 (Biogenex) monoclonal antibodies, which are specific for an extracellular domain of human CD20, were evaluated on human and canine lymphocytes by flow cytometry. Labeling of cells for flow cytometry was performed per the suppliers recommended concentrations (B1) or with neat culture supernatant (1F5). Controls included antibodies of the same isotype with the same direct label or an irrelevant antibody of the same isotype in culture supernatant. Whole blood samples used a commercial lysing reagent (PharmLyse) according to manufacturer's instructions.

Both the B1 and 1F5 antibodies successfully labeled human B-lymphocytes. Neither B1 nor 1F5 demonstrated specific labeling of canine B-cells.

Characterization of CD20 Extracellular Domain 2

The monoclonal antibodies were tested for binding to regions of the canine CD20 extracellular domain 2 (SEQ ID NO:33) using SEQ ID NO:35 APIPYVDIHNCDPA NPSEKNSLSIQYCGSIRSV ("C-terminal polypeptide"). This polypeptide was tested for binding as a linear polypeptide and as a cyclized polypeptide. SEQ ID NO:36 ISHFLK-MENLNLIKAPIPYVDIHNCDPANPSEKNSL ("N-terminal polypeptide") was also tested. The results are shown in Table 2.

TABLE 2

|  | 4F1 | 6C8 | 14A12 | 18D3 |
|---|---|---|---|---|
| SEQ ID NO: 33 | Binding | Binding | Binding | Binding |
| SEQ ID NO: 35 (linear) | Binding | No Binding | Binding | Binding |
| SEQ ID NO: 35 (cyclized) | Binding | No Binding | Binding | Binding |
| SEQ ID NO: 36 | No Binding | Binding | No Binding | No Binding |

The results in Table 2 show that while all four monoclonal antibodies recognize the full-length canine CD20 extracellular domain 2 peptide (SEQ ID NO:33), the epitope recognized by 6C8 is in the amino-terminal portion of the extracellular domain 2, while the epitope(s) recognized by 4F1, 14A12 and 18D3 is/are in the carboxy-terminal portion of the extracellular domain 2.

I claim:

1. An isolated antibody or antigen-binding portion thereof that specifically binds canine CD20, wherein the antibody comprises:
   (i) a VH CDR1 of SEQ ID NO:9, a VH CDR2 of SEQ ID NO:10, VH CDR3 of SEQ ID NO:11, a VL CDR1 of SEQ ID NO:21, a VL CDR2 of SEQ ID NO:22, and a VL CDR3 of SEQ ID NO:23;
   (ii) a VH CDR1 of SEQ ID NO:12, a VH CDR2 of SEQ ID NO:13, VH CDR3 of SEQ ID NO:14, a VL CDR1 of SEQ ID NO:24, a VL CDR2 of SEQ ID NO:25, and a VL CDR3 of SEQ ID NO:26;
   (iii) a VH CDR1 of SEQ ID NO:15, a VH CDR2 of SEQ ID NO:16, VH CDR3 of SEQ ID NO:17, a VL CDR1 of SEQ ID NO:27, a VL CDR2 of SEQ ID NO:28, and a VL CDR3 of SEQ ID NO:29; or
   (iv) a VH CDR1 of SEQ ID NO:18, a VH CDR2 of SEQ ID NO:19, VH CDR3 of SEQ ID NO:20, a VL CDR1 of SEQ ID NO:30, a VL CDR2 of SEQ ID NO:31, and a VL CDR3 of SEQ ID NO:32.

2. The isolated antibody or antigen-binding portion thereof of claim 1, wherein the antibody or antigen-binding portion thereof is a monoclonal antibody, a polyclonal antibody, a chimeric antibody, a humanized antibody, a synthetic antibody, a single chain antibody, a diabody, a caninized antibody, a canine antibody, a human antibody, or a CDR-grafted antibody.

3. The isolated antibody or antigen-binding portion thereof of claim 1, wherein (i) the antibody or antigen-binding portion thereof comprising a VH CDR1 of SEQ ID NO:9, a VH CDR2 of SEQ ID NO:10, VH CDR3 of SEQ ID NO:11, comprises a VL amino acid sequence of SEQ ID NO:5;
   (ii) the antibody or antigen-binding portion thereof comprising a VH CDR1 of SEQ ID NO:12, a VH CDR2 of SEQ ID NO:13, VH CDR3 of SEQ ID NO:14, comprises a VL amino acid sequence of SEQ ID NO:6;
   (iii) the antibody or antigen-binding portion thereof comprising a VH CDR1 of SEQ ID NO:15, a VH CDR2 of SEQ ID NO:16, VH CDR3 of SEQ ID NO:17, comprises a VL amino acid sequence of SEQ ID NO:7;
   (iv) the antibody or antigen-binding portion thereof comprising a VH CDR1 of SEQ ID NO:18, a VH CDR2 of SEQ ID NO:19, VH CDR3 of SEQ ID NO:20, comprises a VL amino acid sequence of SEQ ID NO:8.

4. The isolated antibody or antigen-binding portion thereof of claim 1, wherein said (i) antibody or antigen-binding portion thereof comprising a VL CDR1 of SEQ ID NO:21, a VL CDR2 of SEQ ID NO:22, and a VL CDR3 of SEQ ID NO:23 comprises a VH amino acid sequence of SEQ ID NO:1;
   (ii) antibody or antigen-binding portion thereof comprising a VL CDR1 of SEQ ID NO:24, a VL CDR2 of SEQ ID NO:25, and a VL CDR3 of SEQ ID NO:26 comprises a VH amino acid sequence of SEQ ID NO:2;
   (iii) antibody or antigen-binding portion thereof comprising a VL CDR1 of SEQ ID NO:27, a VL CDR2 of SEQ ID NO:28, and a VL CDR3 of SEQ ID NO:29 comprises a VH amino acid sequence of SEQ ID NO:3;
   (iv) antibody or antigen-binding portion thereof comprising a VL CDR1 of SEQ ID NO:30, a VL CDR2 of SEQ ID NO:31, and a VL CDR3 of SEQ ID NO:32 comprises a VH amino acid sequence of SEQ ID NO:4.

5. A composition comprising the antibody or antigen-binding portion thereof of claim 1 and a pharmaceutically acceptable carrier.

6. The isolated antibody or antigen-binding portion thereof of claim 1, wherein the antibody or antigen-binding portion thereof is an IgG1, an IgG2, an IgG2a, an IgG2b, an IgG3, or an IgG4.

7. The isolated antibody or antigen-binding portion thereof of claim 1, wherein the antibody or antigen-binding portion thereof specifically binds canine CD20 with an affinity ($K_d$) of at least about $10^{-6}$ M.

8. The isolated antibody or antigen-binding portion thereof of claim 1, wherein said antibody or antigen-binding portion thereof induces apoptosis of CD20+cells.

9. The isolated antibody or antigen-binding portion thereof of claim 1, wherein the antibody or antigen-binding portion thereof comprises the same heavy and light chain polypeptide sequences as an antibody produced by hybridoma ATCC number PTA-9433 (4F1), ATCC number PTA-9434 (6C8), ATCC number PTA-9435 (14A12), or ATCC number PTA-9436 (18D3).

10. The antibody or antigen-binding portion thereof of claim 1, wherein the antibody is produced by the hybridoma cell line having ATCC number PTA-9433 (4F1), ATCC number PTA-9434 (6C8), ATCC number PTA-9435 (14A12), or ATCC number PTA-9436 (18D3).

11. An isolated cell of hybridoma ATCC number PTA-9433 (4F1), ATCC number PTA-9434 (6C8), ATCC number PTA-9435 (14A12), or ATCC number PTA-9436 (18D3).

12. The isolated antibody or antigen-binding portion thereof of claim 1, wherein said antibody or antigen-binding portion thereof specifically binds to the surface of canine lymphocytes.

* * * * *

SEQUENCE LISTING

```
<160> NUMBER OF SEQ ID NOS: 36

<210> SEQ ID NO 1
<211> LENGTH: 151
<212> TYPE: PRT
<213> ORGANISM: Mus musculus
<220> FEATURE:
<221> NAME/KEY: MISC_FEATURE
<222> LOCATION: (7)..(7)
<223> OTHER INFORMATION: X stands for I or M
<220> FEATURE:
<221> NAME/KEY: MISC_FEATURE
<222> LOCATION: (8)..(8)
<223> OTHER INFORMATION: X stands for L or F
<220> FEATURE:
<221> NAME/KEY: MISC_FEATURE
<222> LOCATION: (143)..(143)
<223> OTHER INFORMATION: X stands for A or V

<400> SEQUENCE: 1

Met Gly Trp Ser Tyr Ile Xaa Xaa Phe Leu Val Ala Thr Ala Thr Asp
 1               5                  10                  15

Val His Ser Gln Val Gln Leu Gln Pro Gly Ala Glu Leu Val Lys
                20                  25                  30

Pro Gly Ala Ser Val Lys Leu Ser Cys Lys Ala Ser Gly Tyr Ile Phe
            35                  40                  45

Thr Thr Tyr Trp Met Asn Trp Val Lys Gln Arg Pro Gly Gln Gly Leu
```

```
                    50                  55                  60
Glu Trp Ile Gly Glu Ile Ser Pro Ser Asp Gly Arg Ile Asn Tyr Asn
 65                  70                  75                  80

Glu Lys Phe Lys Asn Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Asp Ser Tyr Trp Gly Gln Gly Thr Leu Val Thr
        115                 120                 125

Val Ser Ala Ala Lys Thr Thr Pro Pro Ser Val Tyr Pro Leu Xaa Pro
    130                 135                 140

Gly Ser Leu Gly Arg Ala Asn
145                 150
```

```
<210> SEQ ID NO 2
<211> LENGTH: 158
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: X stands for E or K
<220> FEATURE:
<221> NAME/KEY: MISC_FEATURE
<222> LOCATION: (3)..(3)
<223> OTHER INFORMATION: X stands for C or W
<220> FEATURE:
<221> NAME/KEY: MISC_FEATURE
<222> LOCATION: (4)..(4)
<223> OTHER INFORMATION: X stands for S or T
<220> FEATURE:
<221> NAME/KEY: MISC_FEATURE
<222> LOCATION: (8)..(8)
<223> OTHER INFORMATION: X stands for L or F
<220> FEATURE:
<221> NAME/KEY: MISC_FEATURE
<222> LOCATION: (13)..(13)
<223> OTHER INFORMATION: X stands for M or V
<220> FEATURE:
<221> NAME/KEY: MISC_FEATURE
<222> LOCATION: (33)..(33)
<223> OTHER INFORMATION: X stands for P or S
<220> FEATURE:
<221> NAME/KEY: MISC_FEATURE
<222> LOCATION: (44)..(44)
<223> OTHER INFORMATION: X stands for P or S
<220> FEATURE:
<221> NAME/KEY: MISC_FEATURE
<222> LOCATION: (88)..(88)
<223> OTHER INFORMATION: X stands for I or T
<220> FEATURE:
<221> NAME/KEY: MISC_FEATURE
<222> LOCATION: (139)..(139)
<223> OTHER INFORMATION: X stands for V or A
<220> FEATURE:
<221> NAME/KEY: MISC_FEATURE
<222> LOCATION: (148)..(148)
<223> OTHER INFORMATION: X stands for S or P
<220> FEATURE:
<221> NAME/KEY: MISC_FEATURE
<222> LOCATION: (153)..(153)
<223> OTHER INFORMATION: X stands for A or V

<400> SEQUENCE: 2

Met Xaa Xaa Xaa Trp Val Ile Xaa Phe Leu Met Ala Xaa Val Thr Gly
  1               5                  10                  15

Val Asn Ser Glu Val Gln Leu Gln Gln Ser Gly Ala Glu Val Val Lys
             20                  25                  30

Xaa Gly Ala Ser Val Lys Leu Ser Cys Thr Thr Xaa Gly Phe Asn Ile
```

```
                35                  40                  45
Lys Asp Thr Tyr Ile His Trp Val Lys Gln Arg Pro Glu Gln Gly Leu
 50                  55                  60

Glu Trp Ile Gly Arg Ile Asp Pro Ala Asn Gly Tyr Thr Lys Tyr Asp
 65                  70                  75                  80

Pro Glu Phe Gln Gly Lys Ala Xaa Ile Thr Ala Gly Thr Ser Ser Asn
                 85                  90                  95

Thr Ala Tyr Leu Gln Leu Ser Ser Leu Thr Ser Glu Asp Thr Ala Val
                100                 105                 110

Tyr Tyr Cys Ala Arg Trp Gly Asn Gly Asn Pro Tyr Tyr Tyr Ala Met
                115                 120                 125

Asp Tyr Trp Gly Gln Gly Thr Ser Val Thr Xaa Ser Ser Ala Thr Thr
130                 135                 140

Thr Ala Pro Xaa Val Tyr Pro Leu Xaa Pro Gly Ser Leu Gly
145                 150                 155
```

```
<210> SEQ ID NO 3
<211> LENGTH: 148
<212> TYPE: PRT
<213> ORGANISM: Mus musculus
<220> FEATURE:
<221> NAME/KEY: MISC_FEATURE
<222> LOCATION: (139)..(139)
<223> OTHER INFORMATION: X stands for S or P
<220> FEATURE:
<221> NAME/KEY: MISC_FEATURE
<222> LOCATION: (142)..(142)
<223> OTHER INFORMATION: X stands for P or Q
<220> FEATURE:
<221> NAME/KEY: MISC_FEATURE
<222> LOCATION: (144)..(144)
<223> OTHER INFORMATION: X stands for A or V

<400> SEQUENCE: 3

Ser Leu Leu Tyr Leu Leu Thr Ala Leu Pro Gly Ile Leu Ser Glu Val
 1               5                  10                  15

Gln Leu Gln Glu Ser Gly Pro Ser Leu Val Lys Pro Ser Gln Thr Leu
                20                  25                  30

Ser Leu Thr Cys Ser Val Thr Gly Asp Ser Ile Thr Ser Gly Tyr Trp
                35                  40                  45

Asn Trp Ile Arg Gln Phe Pro Gly Asn Lys Leu Glu Tyr Met Gly Tyr
 50                  55                  60

Ile Ser Tyr Ser Gly Ile Thr Tyr Tyr Asn Pro Ser Leu Lys Ser Arg
 65                  70                  75                  80

Ile Ser Ile Thr Arg Asp Thr Ser Lys Asn Gln Tyr Tyr Leu Gln Leu
                 85                  90                  95

Asn Ser Leu Thr Thr Glu Asp Thr Ala Thr Tyr Tyr Cys Ala Arg Ser
                100                 105                 110

Leu Tyr Asp Tyr Val Gly Phe Ala Tyr Trp Gly Gln Gly Thr Leu Val
                115                 120                 125

Thr Val Ser Ala Ala Lys Thr Thr Pro Pro Xaa Val Tyr Xaa Leu Xaa
130                 135                 140

Pro Gly Ser Leu
145
```

```
<210> SEQ ID NO 4
<211> LENGTH: 154
<212> TYPE: PRT
<213> ORGANISM: Mus musculus
<220> FEATURE:
```

```
<221> NAME/KEY: MISC_FEATURE
<222> LOCATION: (2)..(2)
<223> OTHER INFORMATION: X stands for E or K
<220> FEATURE:
<221> NAME/KEY: MISC_FEATURE
<222> LOCATION: (7)..(7)
<223> OTHER INFORMATION: X stands for I of F
<220> FEATURE:
<221> NAME/KEY: MISC_FEATURE
<222> LOCATION: (141)..(141)
<223> OTHER INFORMATION: X stands for S or P

<400> SEQUENCE: 4

Met Xaa Trp Ser Trp Val Xaa Leu Phe Leu Val Ala Thr Ala Ile Gly
1               5                   10                  15

Val His Ser Gln Val Gln Leu Gln Gln Ser Gly Ala Glu Leu Val Lys
            20                  25                  30

Pro Gly Ala Ser Val Lys Met Ser Cys Lys Ala Phe Gly Tyr Thr Phe
        35                  40                  45

Thr Thr Tyr Pro Ile Glu Trp Met Lys Gln Asn His Gly Lys Ser Leu
    50                  55                  60

Glu Trp Ile Gly Asn Phe His Pro Tyr Asn Asp Asp Thr Lys Tyr Asn
65                  70                  75                  80

Glu Lys Phe Lys Gly Lys Ala Lys Leu Thr Val Glu Lys Ser Ser Ser
                85                  90                  95

Thr Val Tyr Leu Glu Leu Ser Arg Leu Thr Ser Asp Asp Ser Ala Val
            100                 105                 110

Tyr Tyr Cys Ala Met Gly Tyr Tyr Phe Asp Tyr Trp Gly Gln Gly Thr
        115                 120                 125

Thr Leu Thr Val Ser Ser Ala Lys Thr Thr Pro Pro Xaa Val Tyr Pro
    130                 135                 140

Leu Val Pro Gly Ser Leu Gly Arg Ala Asn
145                 150

<210> SEQ ID NO 5
<211> LENGTH: 131
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: X stands for I or T
<220> FEATURE:
<221> NAME/KEY: MISC_FEATURE
<222> LOCATION: (62)..(62)
<223> OTHER INFORMATION: X stands for S or P
<220> FEATURE:
<221> NAME/KEY: MISC_FEATURE
<222> LOCATION: (71)..(71)
<223> OTHER INFORMATION: X stands for G or S
<220> FEATURE:
<221> NAME/KEY: MISC_FEATURE
<222> LOCATION: (92)..(92)
<223> OTHER INFORMATION: X stands for H or Y

<400> SEQUENCE: 5

Asp Xaa Val Met Ser Gln Ser Pro Ser Ser Leu Ala Val Ser Leu Gly
1               5                   10                  15

Glu Lys Ile Thr Met Ser Cys Lys Ser Ser Gln Ser Leu Leu Tyr Ser
            20                  25                  30

Ser Asn Gln Lys Ser Tyr Leu Ala Trp Tyr Gln Gln Lys Pro Gly Gln
        35                  40                  45

Ser Pro Glu Leu Leu Ile Tyr Trp Ala Ser Thr Arg Asp Xaa Gly Val
    50                  55                  60
```

```
Pro Asp Arg Phe Thr Gly Xaa Gly Ser Gly Thr Asp Phe Thr Leu Thr
 65                  70                  75                  80

Ile Ser Ser Val Lys Ala Glu Asp Leu Ala Val Xaa Phe Cys Gln Gln
                 85                  90                  95

Tyr Tyr Thr Tyr Pro Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Lys Leu Gly
    130

<210> SEQ ID NO 6
<211> LENGTH: 134
<212> TYPE: PRT
<213> ORGANISM: Mus musculus
<220> FEATURE:
<221> NAME/KEY: MISC_FEATURE
<222> LOCATION: (31)..(31)
<223> OTHER INFORMATION: X stands for C or Y

<400> SEQUENCE: 6

Asp Ile Val Met Ser Gln Ser Pro Ser Ser Leu Ala Val Ser Val Gly
 1               5                  10                  15

Glu Lys Val Thr Val Ser Cys Lys Ser Ser Gln Thr Leu Leu Xaa Ser
                 20                  25                  30

Ser Asn Gln Lys Asn Tyr Leu Ala Trp Tyr Gln Gln Lys Pro Gly Gln
            35                  40                  45

Ser Pro Asn Leu Leu Ile Tyr Ser Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Asn Leu Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys Arg Ala Asp Ala Ala Pro Thr Val Ser Ile Phe Pro Pro Ser Ser
        115                 120                 125

Lys Leu Gly Lys Gly Glu
    130

<210> SEQ ID NO 7
<211> LENGTH: 126
<212> TYPE: PRT
<213> ORGANISM: Mus musculus

<400> SEQUENCE: 7

Leu Val Asp Met Asp Phe Gln Val Gln Ile Ile Ser Phe Leu Leu Ile
 1               5                  10                  15

Ser Ala Ser Gly Gln Ile Val Leu Thr Gln Ser Pro Ala Ile Met Ser
                 20                  25                  30

Ala Ser Pro Gly Glu Arg Val Thr Val Thr Phe Ser Ala Arg Ser Ser
            35                  40                  45

Val Arg Ser Ser Tyr Leu Tyr Leu Tyr Gln Gln Lys Pro Gly Ser Ser
 50                  55                  60

Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
```

-continued

```
                    85                  90                  95
Ser Ser Met Glu Thr Glu Asp Ala Ala Thr Phe Tyr Cys Gln Gln Tyr
                100                 105                 110

Ser Gly Tyr Pro Ser Arg Ser Val Leu Gly Pro Ser Trp Ser
                115                 120                 125

<210> SEQ ID NO 8
<211> LENGTH: 149
<212> TYPE: PRT
<213> ORGANISM: Mus musculus
<220> FEATURE:
<221> NAME/KEY: MISC_FEATURE
<222> LOCATION: (4)..(4)
<223> OTHER INFORMATION: X stands for I or T
<220> FEATURE:
<221> NAME/KEY: MISC_FEATURE
<222> LOCATION: (5)..(5)
<223> OTHER INFORMATION: X stands for P or S
<220> FEATURE:
<221> NAME/KEY: MISC_FEATURE
<222> LOCATION: (7)..(7)
<223> OTHER INFORMATION: X stands for I or L
<220> FEATURE:
<221> NAME/KEY: MISC_FEATURE
<222> LOCATION: (8)..(8)
<223> OTHER INFORMATION: X stands for F or L

<400> SEQUENCE: 8

Met Ala Trp Xaa Xaa Leu Xaa Xaa Ser Leu Leu Ala Leu Ser Ser Gly
1               5                   10                  15

Ala Ile Ser Gln Ala Val Val Thr Gln Glu Ser Ala Leu Thr Thr Ser
                20                  25                  30

Pro Gly Glu Thr Val Thr Leu Thr Cys Arg Ser Ser Thr Gly Ala Val
                35                  40                  45

Thr Thr Ser Asn Tyr Ala Asn Trp Val Gln Glu Lys Pro Asp His Leu
            50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
                100                 105                 110

Tyr Ser Asn His Trp Val Phe Gly Gly Gly Thr Lys Leu Thr Val Leu
                115                 120                 125

Gly Gln Pro Lys Ser Ser Pro Ser Val Thr Leu Phe Pro Pro Ser Thr
                130                 135                 140

Glu Glu Leu Ser Leu
145

<210> SEQ ID NO 9
<211> LENGTH: 9
<212> TYPE: PRT
<213> ORGANISM: Mus musculus

<400> SEQUENCE: 9

Tyr Ile Phe Thr Thr Tyr Trp Met Asn
1               5

<210> SEQ ID NO 10
<211> LENGTH: 17
<212> TYPE: PRT
<213> ORGANISM: Mus musculus
```

```
<400> SEQUENCE: 10

Glu Ile Ser Pro Ser Asp Gly Arg Ile Asn Tyr Asn Glu Lys Phe Lys
1               5                   10                  15
Asn

<210> SEQ ID NO 11
<211> LENGTH: 4
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: Amino acids 1-3 are 6C8 heavy chain CDR3

<400> SEQUENCE: 11

Asp Ser Tyr Trp
1

<210> SEQ ID NO 12
<211> LENGTH: 9
<212> TYPE: PRT
<213> ORGANISM: Mus musculus

<400> SEQUENCE: 12

Phe Asn Ile Lys Asp Thr Tyr Ile His
1               5

<210> SEQ ID NO 13
<211> LENGTH: 17
<212> TYPE: PRT
<213> ORGANISM: Mus musculus

<400> SEQUENCE: 13

Arg Ile Asp Pro Ala Asn Gly Tyr Thr Lys Tyr Asp Pro Glu Phe Gln
1               5                   10                  15
Gly

<210> SEQ ID NO 14
<211> LENGTH: 13
<212> TYPE: PRT
<213> ORGANISM: Mus musculus

<400> SEQUENCE: 14

Trp Gly Asn Gly Asn Pro Tyr Tyr Tyr Ala Met Asp Tyr
1               5                   10

<210> SEQ ID NO 15
<211> LENGTH: 9
<212> TYPE: PRT
<213> ORGANISM: Mus musculus

<400> SEQUENCE: 15

Asp Ser Ile Thr Ser Gly Tyr Trp Asn
1               5

<210> SEQ ID NO 16
<211> LENGTH: 16
<212> TYPE: PRT
<213> ORGANISM: Mus musculus

<400> SEQUENCE: 16

Tyr Ile Ser Tyr Ser Gly Ile Thr Tyr Tyr Asn Pro Ser Leu Lys Ser
1               5                   10                  15
```

<210> SEQ ID NO 17
<211> LENGTH: 10
<212> TYPE: PRT
<213> ORGANISM: Mus musculus

<400> SEQUENCE: 17

Ser Leu Tyr Asp Tyr Val Gly Phe Ala Tyr
1               5                   10

<210> SEQ ID NO 18
<211> LENGTH: 9
<212> TYPE: PRT
<213> ORGANISM: Mus musculus

<400> SEQUENCE: 18

Tyr Thr Phe Thr Thr Tyr Pro Ile Glu
1               5

<210> SEQ ID NO 19
<211> LENGTH: 17
<212> TYPE: PRT
<213> ORGANISM: Mus musculus

<400> SEQUENCE: 19

Asn Phe His Pro Tyr Asn Asp Asp Thr Lys Tyr Asn Glu Lys Phe Lys
1               5                   10                  15

Gly

<210> SEQ ID NO 20
<211> LENGTH: 6
<212> TYPE: PRT
<213> ORGANISM: Mus musculus

<400> SEQUENCE: 20

Gly Tyr Tyr Phe Asp Tyr
1               5

<210> SEQ ID NO 21
<211> LENGTH: 17
<212> TYPE: PRT
<213> ORGANISM: Mus musculus

<400> SEQUENCE: 21

Lys Ser Ser Gln Ser Leu Leu Tyr Ser Ser Asn Gln Lys Ser Tyr Leu
1               5                   10                  15

Ala

<210> SEQ ID NO 22
<211> LENGTH: 7
<212> TYPE: PRT
<213> ORGANISM: Mus musculus
<220> FEATURE:
<221> NAME/KEY: MISC_FEATURE
<222> LOCATION: (7)..(7)
<223> OTHER INFORMATION: X stands for S or P

<400> SEQUENCE: 22

Trp Ala Ser Thr Arg Asp Xaa
1               5

<210> SEQ ID NO 23
<211> LENGTH: 9
<212> TYPE: PRT
<213> ORGANISM: Mus musculus

<400> SEQUENCE: 23

Gln Gln Tyr Tyr Thr Tyr Pro Tyr Thr
1               5

<210> SEQ ID NO 24
<211> LENGTH: 17
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 24

Lys Ser Ser Gln Thr Leu Leu Xaa Ser Ser Asn Gln Lys Asn Tyr Leu
1               5                   10                  15

Ala

<210> SEQ ID NO 25
<211> LENGTH: 7
<212> TYPE: PRT
<213> ORGANISM: Mus musculus

<400> SEQUENCE: 25

Ser Ala Ser Thr Arg Glu Ser
1               5

<210> SEQ ID NO 26
<211> LENGTH: 9
<212> TYPE: PRT
<213> ORGANISM: Mus musculus

<400> SEQUENCE: 26

Gln Gln Tyr Tyr Ser Tyr Pro Leu Thr
1               5

<210> SEQ ID NO 27
<211> LENGTH: 11
<212> TYPE: PRT
<213> ORGANISM: Mus musculus

<400> SEQUENCE: 27

Ser Ala Arg Ser Ser Val Arg Ser Ser Tyr Leu
1               5                   10

<210> SEQ ID NO 28
<211> LENGTH: 7
<212> TYPE: PRT
<213> ORGANISM: Mus musculus

<400> SEQUENCE: 28

Ser Thr Ser Asn Leu Ala Ser
1               5

<210> SEQ ID NO 29
<211> LENGTH: 9
<212> TYPE: PRT
<213> ORGANISM: Mus musculus

<400> SEQUENCE: 29

Gln Gln Tyr Ser Gly Tyr Pro Ser Arg
1               5

```
<210> SEQ ID NO 30
<211> LENGTH: 13
<212> TYPE: PRT
<213> ORGANISM: Mus musculus

<400> SEQUENCE: 30

Arg Ser Ser Thr Gly Ala Val Thr Thr Ser Asn Tyr Ala
1               5                   10

<210> SEQ ID NO 31
<211> LENGTH: 7
<212> TYPE: PRT
<213> ORGANISM: Mus musculus

<400> SEQUENCE: 31

Gly Thr Asn Asn Arg Ala Pro
1               5

<210> SEQ ID NO 32
<211> LENGTH: 9
<212> TYPE: PRT
<213> ORGANISM: Mus musculus

<400> SEQUENCE: 32

Ala Leu Trp Tyr Ser Asn His Trp Val
1               5

<210> SEQ ID NO 33
<211> LENGTH: 53
<212> TYPE: PRT
<213> ORGANISM: Canis familiaris

<400> SEQUENCE: 33

Asp Ile Phe Asn Ile Thr Ile Ser His Phe Leu Lys Met Glu Asn Leu
1               5                   10                  15

Asn Leu Ile Lys Ala Pro Ile Pro Tyr Val Asp Ile His Asn Cys Asp
            20                  25                  30

Pro Ala Asn Pro Ser Glu Lys Asn Ser Leu Ser Ile Gln Tyr Cys Gly
        35                  40                  45

Ser Ile Arg Ser Val
    50

<210> SEQ ID NO 34
<211> LENGTH: 75
<212> TYPE: PRT
<213> ORGANISM: Artificial Sequence
<220> FEATURE:
<223> OTHER INFORMATION: ED2 of canine CD20 polypeptide and murine T
      cell epitope from ovalbumin

<400> SEQUENCE: 34

Asp Asp Leu Gln Ala Val His Ala Ala His Ala Glu Ile Asn Glu Ala
1               5                   10                  15

Asp His Ile Asp Ile Asp Ile Phe Asn Ile Thr Ile Ser His Phe
            20                  25                  30

Leu Lys Met Glu Asn Leu Asn Leu Ile Lys Ala Pro Ile Pro Tyr Val
            35                  40                  45

Asp Ile His Asn Cys Asp Pro Ala Asn Pro Ser Glu Lys Asn Ser Leu
        50                  55                  60

Ser Ile Gln Tyr Cys Gly Ser Ile Arg Ser Val
65                  70                  75
```

```
<210> SEQ ID NO 35
<211> LENGTH: 33
<212> TYPE: PRT
<213> ORGANISM: Canis familiaris

<400> SEQUENCE: 35

Ala Pro Ile Pro Tyr Val Asp Ile His Asn Cys Asp Pro Ala Asn Pro
1               5                   10                  15

Ser Glu Lys Asn Ser Leu Ser Ile Gln Tyr Cys Gly Ser Ile Arg Ser
            20                  25                  30

Val

<210> SEQ ID NO 36
<211> LENGTH: 36
<212> TYPE: PRT
<213> ORGANISM: Canis familiaris

<400> SEQUENCE: 36

Ile Ser His Phe Leu Lys Met Glu Asn Leu Asn Leu Ile Lys Ala Pro
1               5                   10                  15

Ile Pro Tyr Val Asp Ile His Asn Cys Asp Pro Ala Asn Pro Ser Glu
            20                  25                  30

Lys Asn Ser Leu
            35
```